United States Patent
Kawasaki et al.

(10) Patent No.: US 8,198,281 B2
(45) Date of Patent: Jun. 12, 2012

(54) CRYSTALLINE FORMS OF DIHYDROPYRAZOLOPYRIMIDINONE

(75) Inventors: Masashi Kawasaki, Tsukuba (JP); Hiroo Mizuno, Tsukuba (JP); Toshihiro Sakamoto, Moriya (JP); Kimimasa Suzuki, Tsukuba (JP); Arlene E. McKeown, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 139 days.

(21) Appl. No.: 12/597,012

(22) PCT Filed: Apr. 22, 2008

(86) PCT No.: PCT/US2008/005155
§ 371 (c)(1),
(2), (4) Date: Oct. 22, 2009

(87) PCT Pub. No.: WO2008/133866
PCT Pub. Date: Nov. 6, 2008

(65) Prior Publication Data
US 2010/0124544 A1    May 20, 2010

Related U.S. Application Data

(60) Provisional application No. 61/000,185, filed on Oct. 24, 2007.

(30) Foreign Application Priority Data

Apr. 25, 2007  (JP) .................................. 2007-115448

(51) Int. Cl.
*A61K 31/497* (2006.01)
*A61K 31/519* (2006.01)
*A01N 43/90* (2006.01)
*C07D 487/00* (2006.01)
*C07D 413/00* (2006.01)
*C07D 417/00* (2006.01)
*C07D 419/00* (2006.01)

(52) U.S. Cl. ................ 514/252.16; 514/262.1; 544/262; 544/368

(58) Field of Classification Search ........................ None
See application file for complete search history.

(56) References Cited

U.S. PATENT DOCUMENTS 7,834,019 B2 * 11/2010 Sagara et al. ............ 514/252.16
2007/0254892 A1    11/2007 Sagara

FOREIGN PATENT DOCUMENTS

WO    WO03091255    11/2003
WO    WO2007126122    11/2007

* cited by examiner

*Primary Examiner* — Jeffrey Murray
(74) *Attorney, Agent, or Firm* — Joan E. Switzer

(57) ABSTRACT

The present invention relates to the crystalline forms of 2-allyl-1-[6-(I-hydroxy-1 methylethyl)pyridin-2-yl]-6-{[4-(4-methylpiperazin-1-yl)phenyl]amino}-1,2-dihydro-3H-pyrazolo[3,4-d]pyrimidin-3-one or a salt thereof, which are useful in the field of treatment of various cancers as a kinase inhibitor, especially as a Wee1 kinase inhibitor.

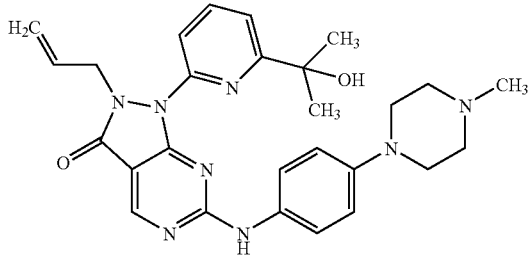

8 Claims, 10 Drawing Sheets

CRYSTALLINE FORMS OF DIHYDROPYRAZOLOPYRIMIDINONE

CROSS REFERENCE TO RELATED APPLICATIONS

This application is a U.S. National Phase application under 35 U.S.C. §371 of PCT Application No. PCT/US2008/005155 filed Apr. 22, 2008, which claims priority from U.S. Provisional Application Ser. No. 61/000,185, filed Oct. 24, 2007, and Japanese Application Serial No. 2007-115448, filed Apr. 25, 2007.

TECHNICAL FIELD

The present invention is useful in the field of medicine. More precisely, the present invention relates to the crystalline forms of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one (Compound A) or a salt thereof, which are useful in the field of treatment of various cancers as a kinase inhibitor, especially as a Wee1 kinase inhibitor.

BACKGROUND ART

Cells have a checkpoint mechanism such that, when the DNA therein is damaged, then the cells temporarily stop the cell cycle and repair the damaged DNA (*Cell Proliferation*, Vol. 33, pp. 261-274). In about a half of human cancers, a cancer-suppressor gene, p53 is mutated or depleted and thereby the cells have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (*The EMBO Journal*, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray or gamma ray (*Cancer Biology & Therapy*, Vol. 3, pp. 305-313; *Cancer Research*, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known are compounds described in US Application 2005/0250836, WO2003/091255, *Cancer Research*, Vol. 61, pp. 8211-8217, or *Bioorg & Med. Chem. Lett.*, Vol. 15, pp. 1931-1935. However, the compounds described in these references quite differ from the compounds of the invention in terms of their structures.

On the other hand, Japanese patent application No. 2006-124208 (filed on Apr. 27, 2006) discloses Compound A per se and a certain solid form thereof, which have an excellent Wee1 kinase-inhibitory effect and are useful in the field of the treatment of cancer.

DISCLOSURE OF INVENTION

Figure 1:
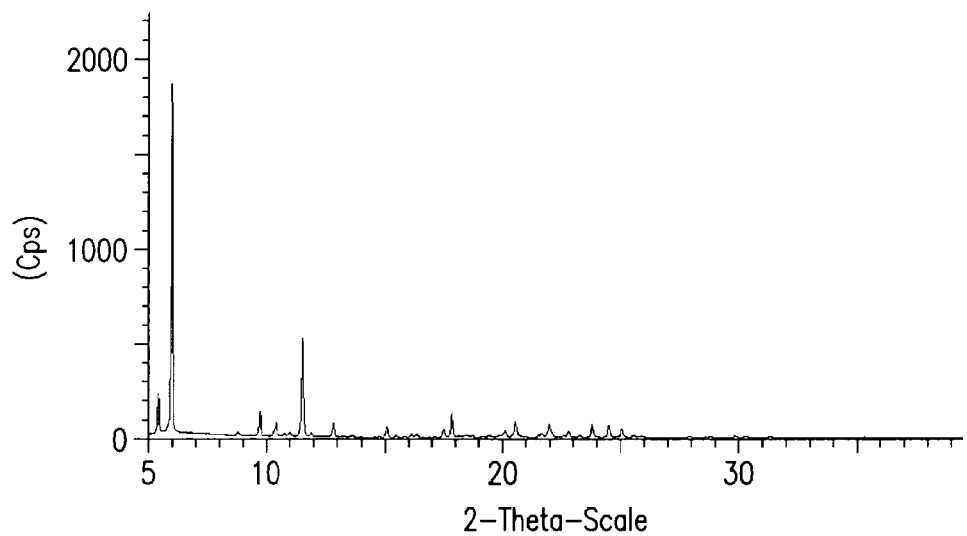
FIG. 1 is the X-ray diffraction (XRPD) pattern for Form G (monohydrate) of Compound A.
Figure 2:
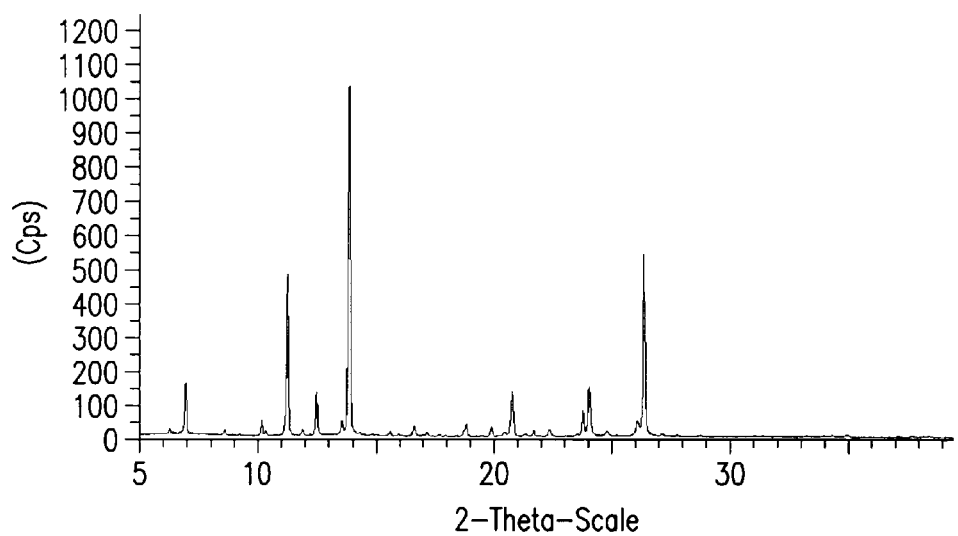
FIG. 2 is the XRPD Pattern for Form A of Compound A.
Figure 3:
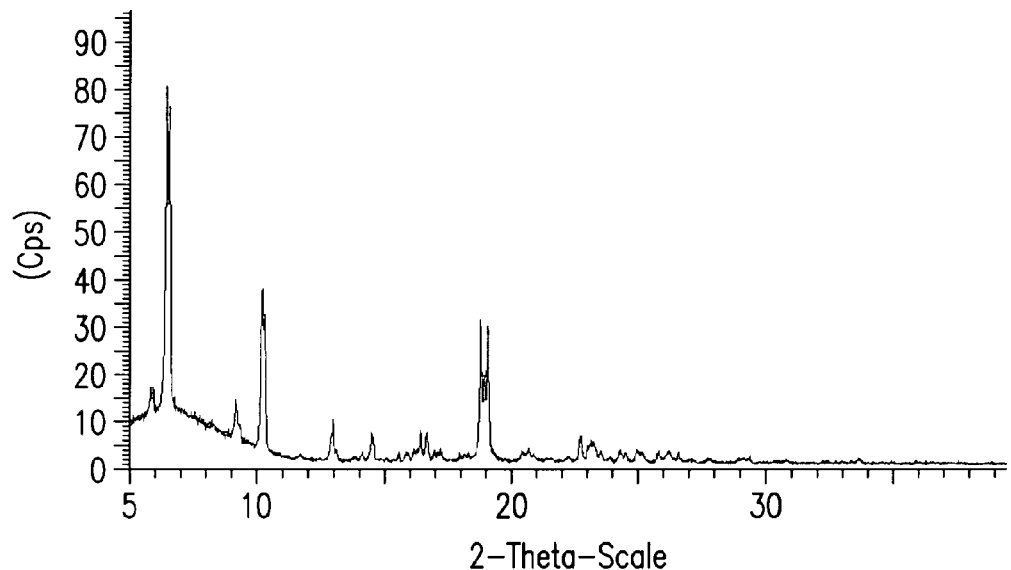
FIG. 3 is the XRPD Pattern for Form B of Compound A.
Figure 4:
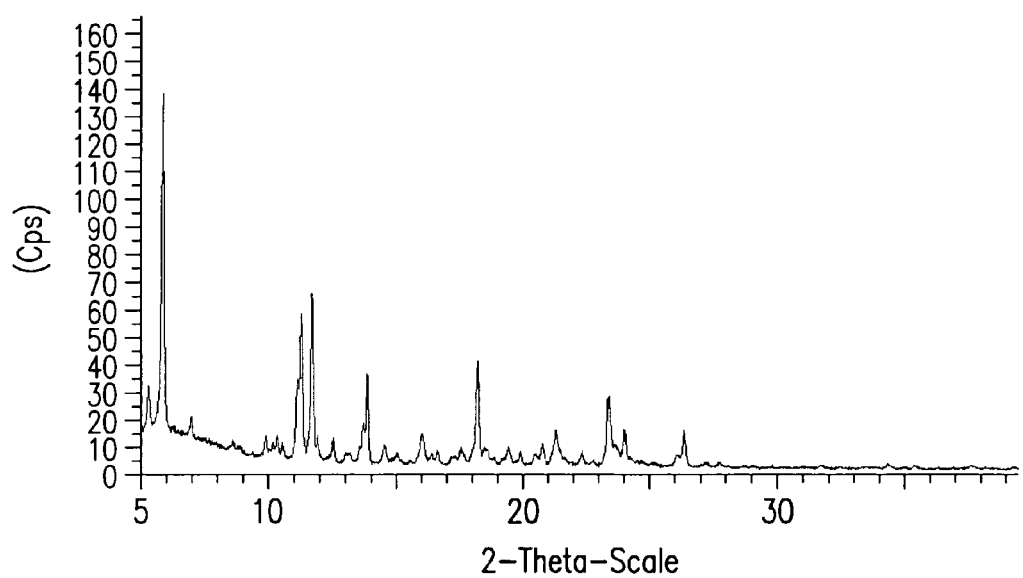
FIG. 4 is the XRPD Pattern for Form C (sesterhydrate) of Compound A.
Figure 5:
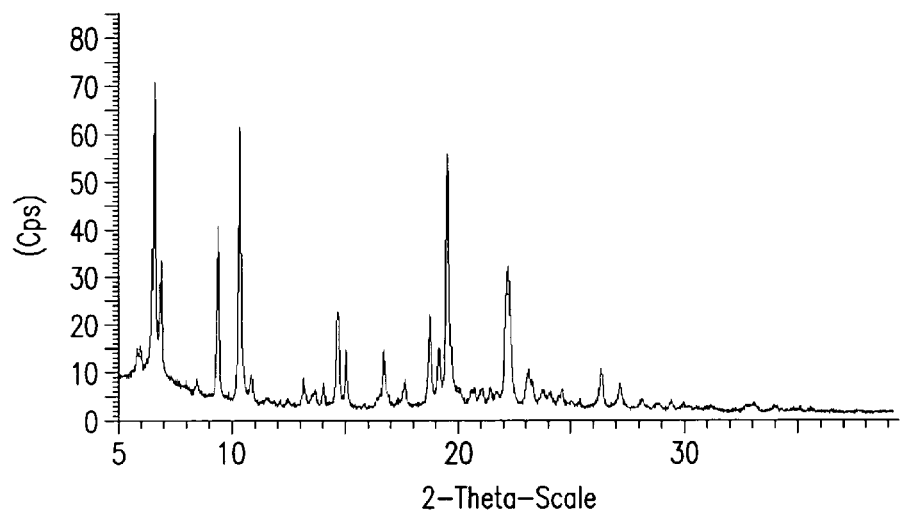
FIG. 5 is the XRPD Pattern for Form D of Compound A.
Figure 6:
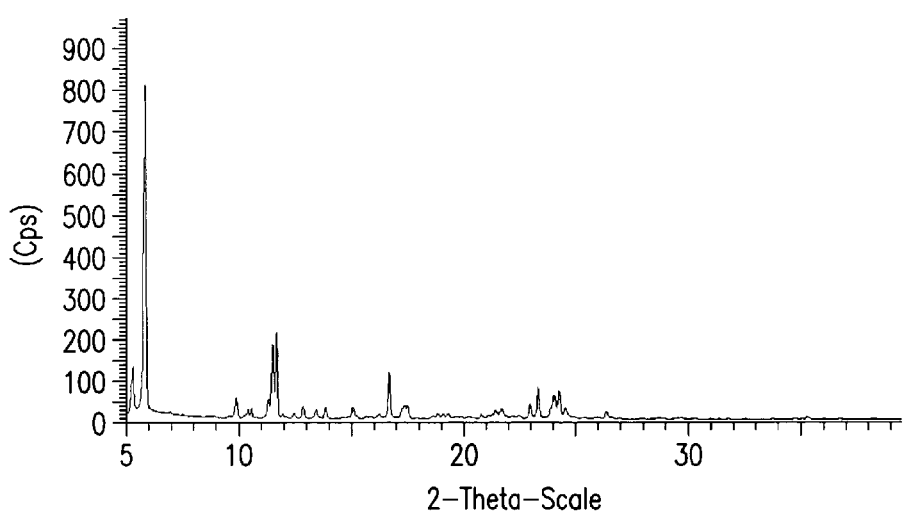
FIG. 6 is the XRPD Pattern for Form H of Compound A.
Figure 7:
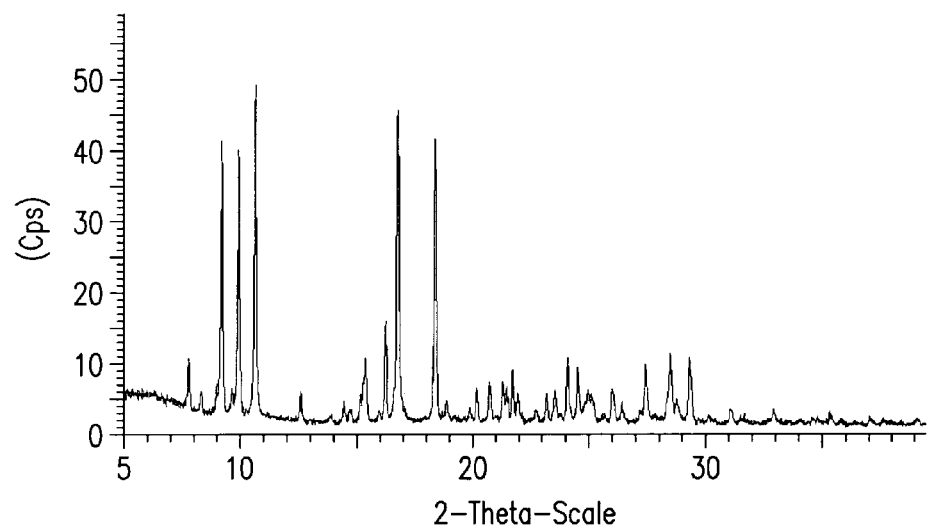
FIG. 7 is the XRPD Pattern for hydrochloride of Compound A.
Figure 8:
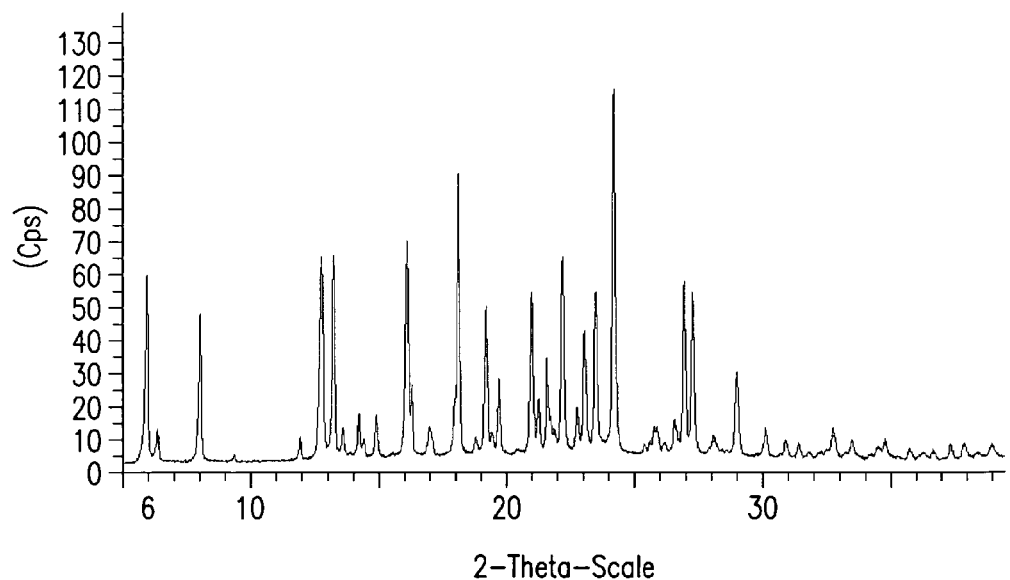
FIG. 8 is the XRPD Pattern for methanesulfonate of Compound A.
Figure 9:
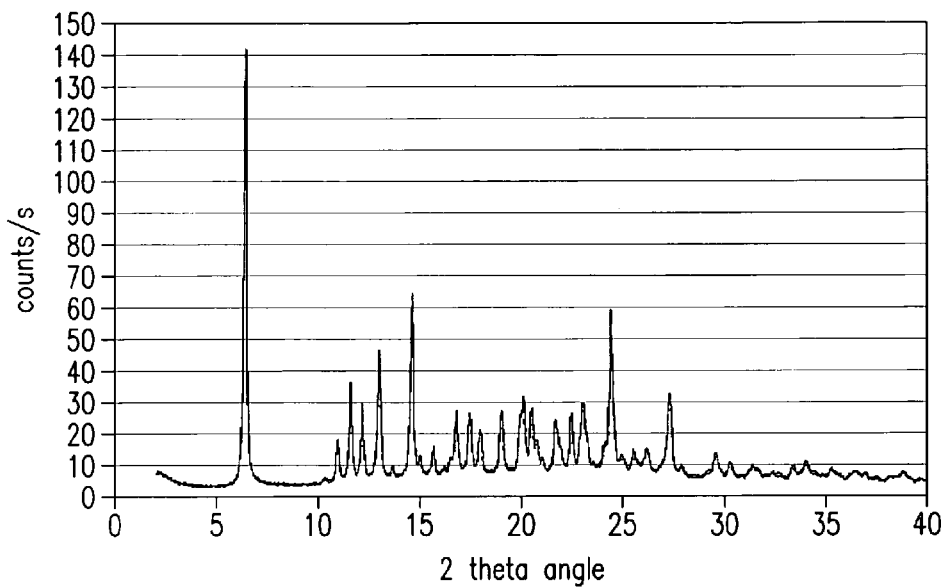
FIG. 9 is the XRPD Pattern for citrate (ethanolate) of Compound A.
Figure 10:
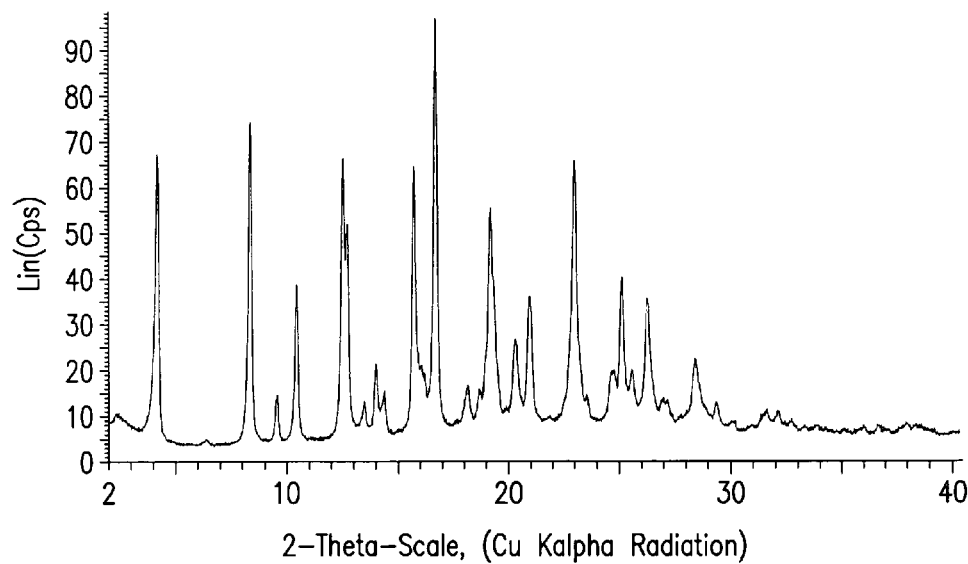
FIG. 10 is the XRPD Pattern for sulfate of Compound A.
Figure 11:
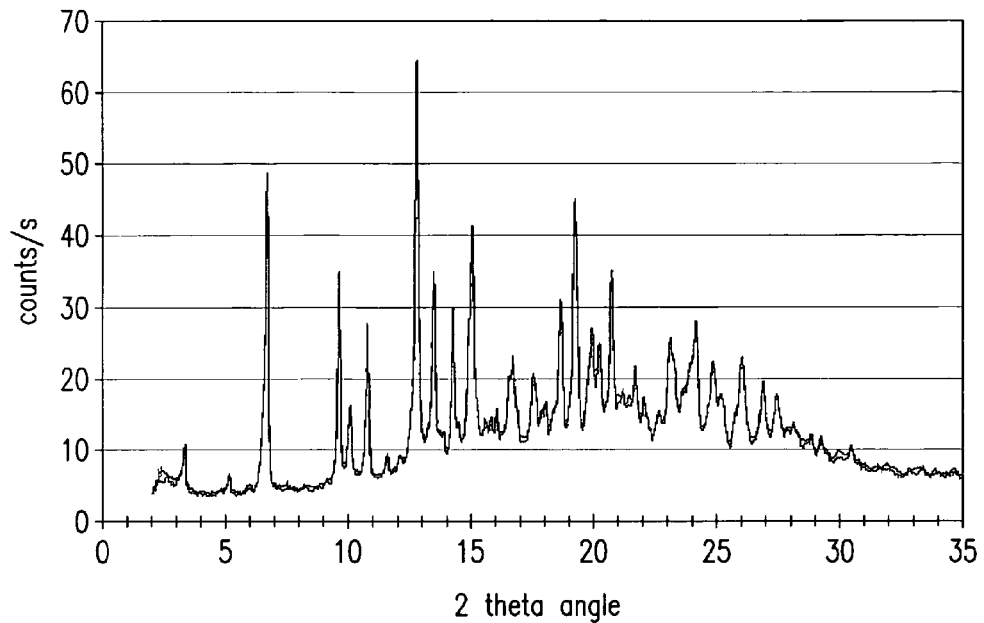
FIG. 11 is the XRPD Pattern for benzenesulfonate (sesquihydrate) of Compound A.
Figure 12:
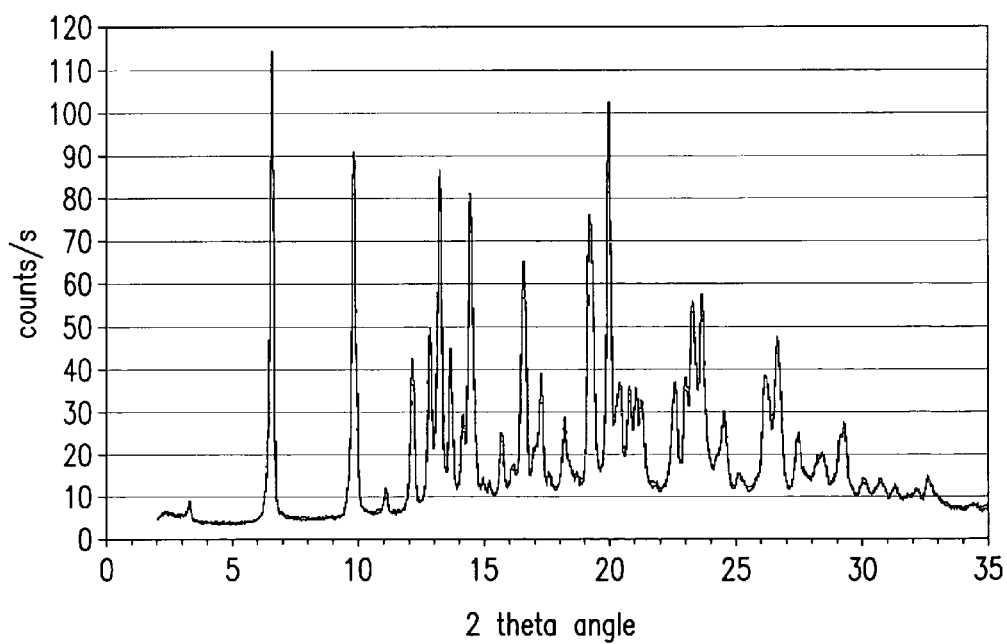
FIG. 12 is the XRPD Pattern for tosylate of Compound A.
Figure 13:
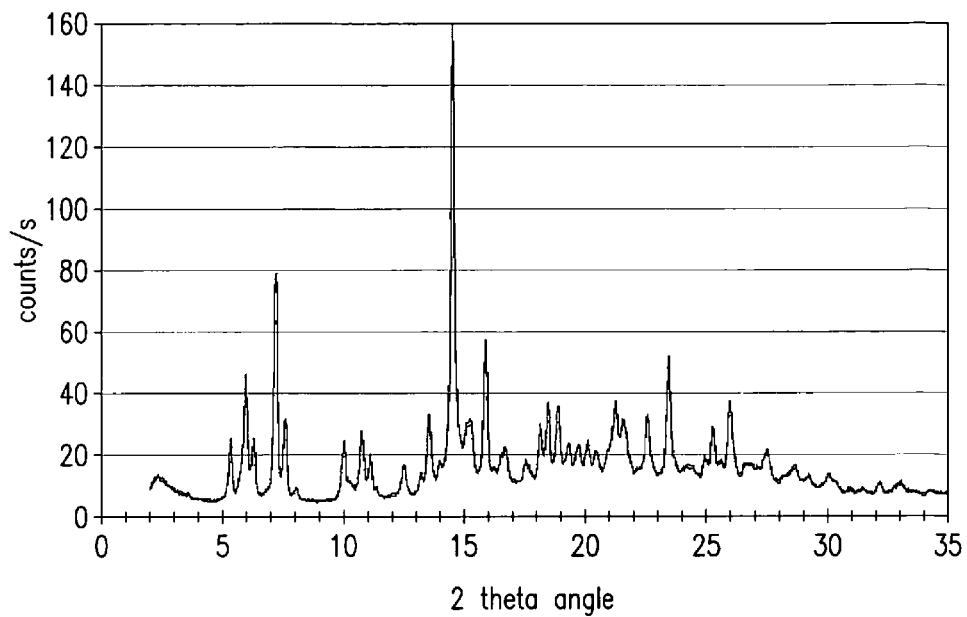
FIG. 13 is the XRPD Pattern for fumarate (hemihydrate) of Compound A.
Figure 14:
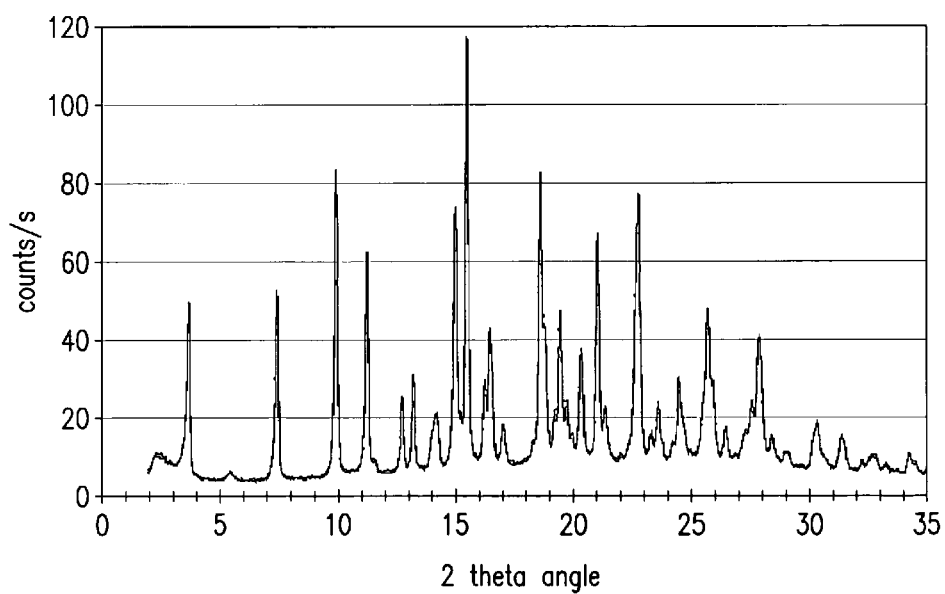
FIG. 14 is the XRPD Pattern for phosphate of Compound A.
Figure 15:
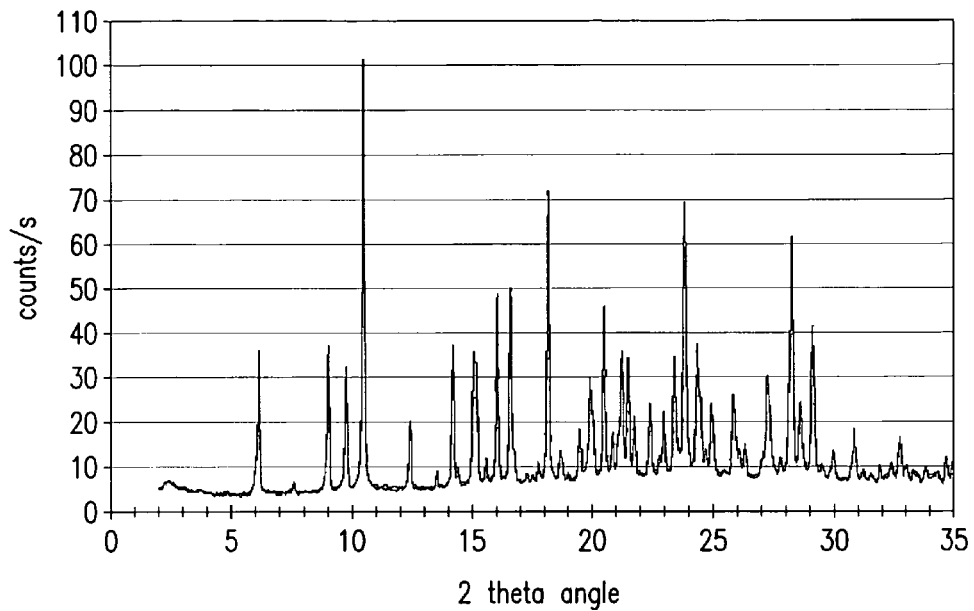
FIG. 15 is the XRPD Pattern for hydrobromide of Compound A.
Figure 16:
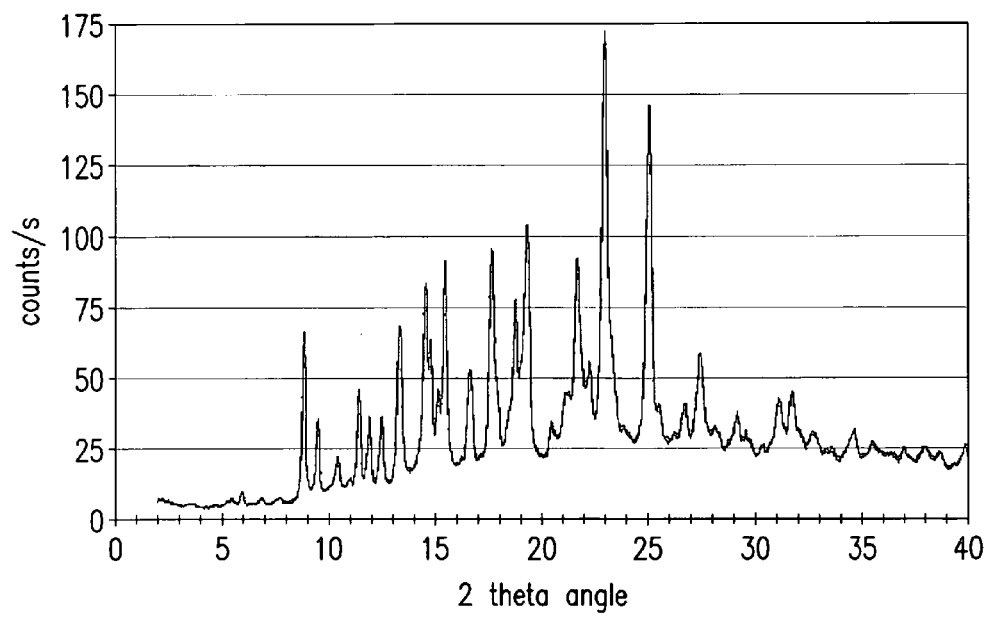
FIG. 16 is the XRPD Pattern for L-malate of Compound A.
Figure 17:
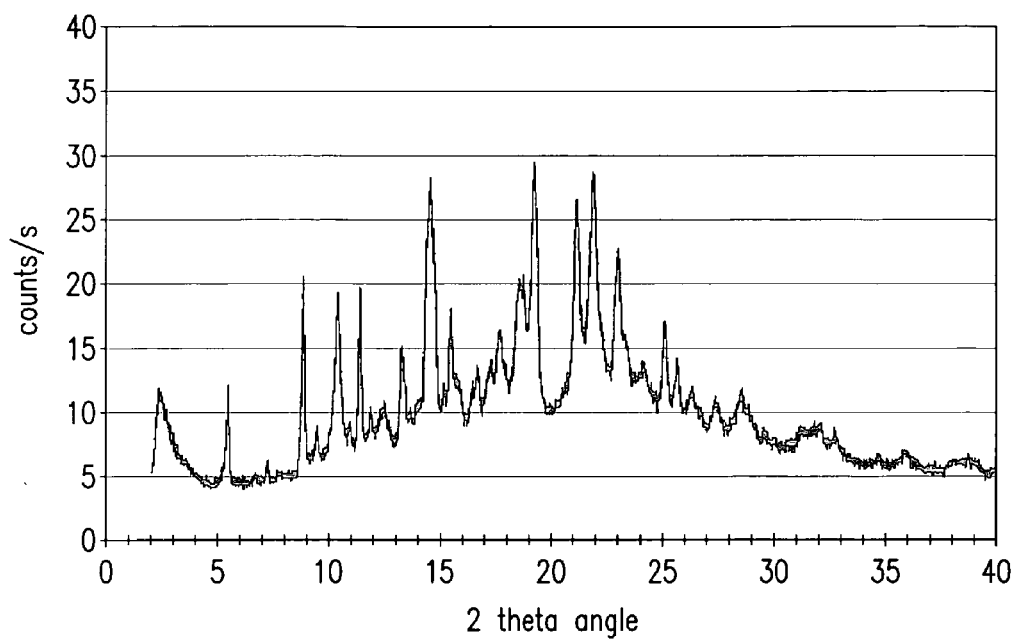
FIG. 17 is the XRPD Pattern for maleate FormA (hemihydrate) of Compound A.
Figure 18:
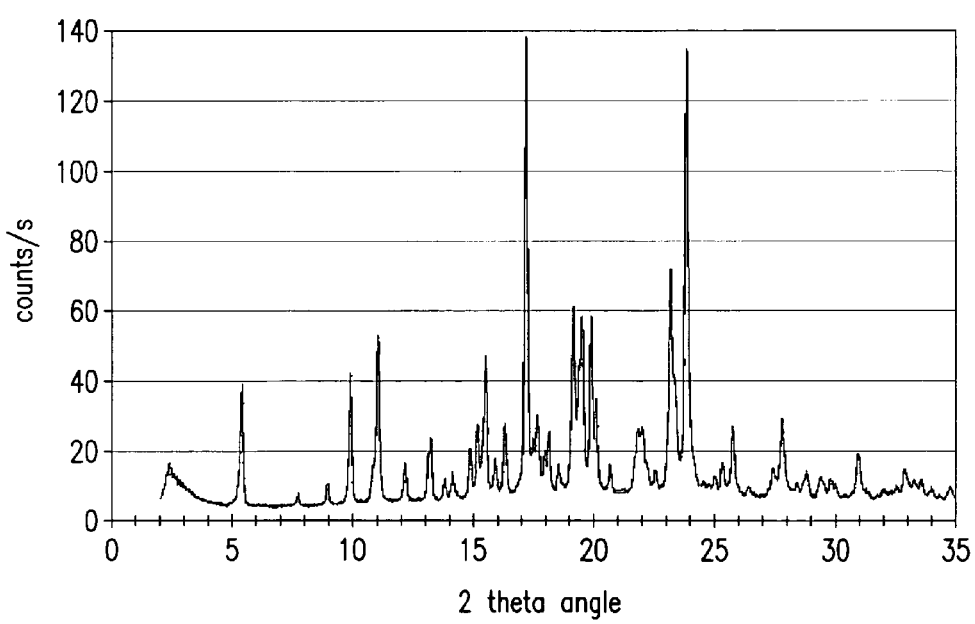
FIG. 18 is the XRPD Pattern for maleate FormB of Compound A.
Figure 19:
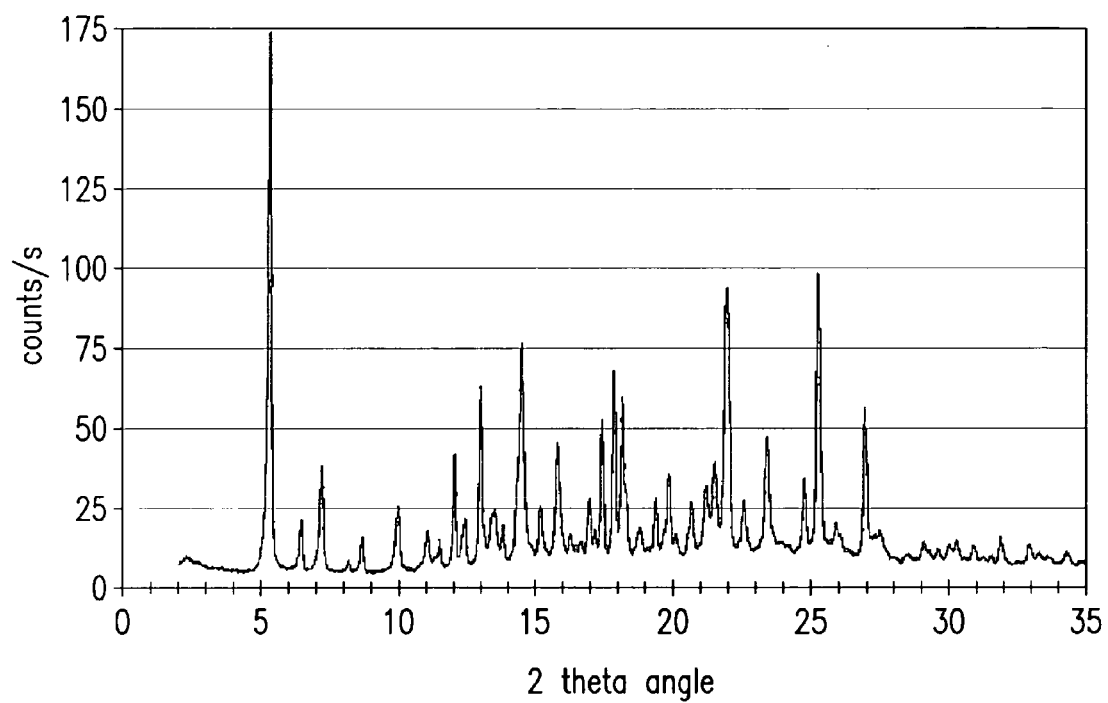
FIG. 19 is the XRPD Pattern for succinate of Compound A.

The invention provides novel crystalline forms of Compound A of structural formula:

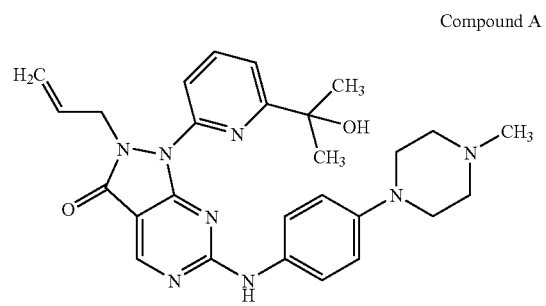

Compound A or a salt thereof, which are selected from the group consisting of Form G (monohydrate), Form B, Form C (sesterhydrate), hydrochloride, methanesulfonate, citrate (ethanolate), sulfate, benzenesulfonate (sesquihydrate), tosylate, fumarate (hemihydrate), phosphate, hydrobromide, L-malate, maleate FormA (hemihydrate), maleate FormB and succinate.

The novel crystalline forms of Compound A or a salt thereof, especially Form G, can be provided stably and constantly from the standpoint of the manufacturing process, and they are useful in the field of the treatment of cancer.

The novel crystalline forms of Compound A or a salt thereof, as well as Compound A per se, have a kinase-inhibitory effect, especially a Wee1 kinase-inhibitory effect, and are therefore useful as pharmaceutical agents for the treatment of various cancers such as brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

In particular, the novel crystalline forms of Compound A or a salt thereof, as well as Compound A per se, are useful as pharmaceutical agents, for example, for the treatment of breast cancer, lung cancer, pancreatic cancer, colon cancer, ovarian cancer, acute leukemia, chronic lymphatic leukemia, chronic myelocytic leukemia, Hodgkin's lymphoma.

The term "Compound A" as referred to herein means a compound of the above-described chemical structural formula and includes any amorphous form, polymorphic crystalline forms, hydrate, solvate and the mixture thereof.

Form G is a crystalline monohydrate of Compound A.

In one aspect, Form G is identified by an X-ray powder diffraction pattern, obtained using Cu K alpha radiation, containing the following angle 2 theta values: 5.4°, 5.9° and 11.5°.

In another aspect, Form G is identified by an X-ray powder diffraction pattern, obtained using Cu K alpha radiation, containing the following angle 2 theta values: 5.4°, 5.9° and 11.5°, and at least one angle 2 theta value selected from the group consisting of: 9.7°, 12.8°, 17.8°, 20.5°, 22.0°, 23.8°, 24.5° and 25.0°.

In another aspect, Form G is identified by an X-ray powder diffraction pattern, obtained using Cu K alpha radiation, containing the following angle 2 theta values: 5.4°, 5.9°, 11.5° and 9.7°.

Form B is a polymorphic crystalline form of Compound A.

In one aspect, Form B is identified by an X-ray powder diffraction pattern, obtained using Cu K alpha radiation, containing the following angle 2 theta values: 6.4° and 6.5°.

In another aspect, Form B is identified by an X-ray powder diffraction pattern, obtained using Cu K alpha radiation, containing the following angle 2 theta values: 6.4° and 6.5°, and at least one angle 2 theta value selected from the group consisting of: 9.1°, 10.2°, 12.9°, 18.8° and 19.0°.

In another aspect, Form B is identified by an X-ray powder diffraction pattern, obtained using Cu K alpha radiation, containing the following angle 2 theta values: 6.4°, 6.5°, and 10.2°.

Form C is a crystalline sesterhydrate of Compound A.

In one aspect, Form C is identified by an X-ray powder diffraction pattern, obtained using Cu K alpha radiation, containing the following angle 2 theta values: 5.8°, 11.2°, 11.6° and 18.2°.

In another aspect, Form C is identified by an X-ray powder diffraction pattern, obtained using Cu K alpha radiation, containing the following angle 2 theta values: 5.8°, 11.2°, 11.6° and 18.2°, and at least one angle 2 theta value selected from the group consisting of: 5.2°, 13.8° and 23.4°.

In another aspect, Form C is identified by an X-ray powder diffraction pattern, obtained using Cu K alpha radiation, containing the following angle 2 theta values: 5.8°, 11.2°, 11.6°, 18.2° and 13.8°.

The hydrochloride is a crystalline salt of Compound A.

In one aspect, the hydrochloride is identified by an X-ray powder diffraction pattern, obtained using Cu K alpha radiation, containing the following angle 2 theta values: 10.6° and 16.7°.

In another aspect, the hydrochloride is identified by an X-ray powder diffraction pattern, obtained using Cu K alpha radiation, containing the following angle 2 theta values: 10.6° and 16.7°, and at least one angle 2 theta value selected from the group consisting of: 9.2°, 9.9°, 16.2° and 18.3°.

In another aspect, the hydrochloride is identified by an X-ray powder diffraction pattern, obtained using Cu K alpha radiation, containing the following angle 2 theta values: 10.6°, 16.7° and 18.3°.

The methanesulfonate is a crystalline salt of Compound A.

In one aspect, the methanesulfonate is identified by an X-ray powder diffraction pattern, obtained using Cu K alpha radiation, containing the following angle 2 theta values: 8.0° and 18.1°.

In another aspect, the methanesulfonate is identified by an X-ray powder diffraction pattern, obtained using Cu K alpha radiation, containing the following angle 2 theta values: 8.0° and 18.1°, and at least one angle 2 theta value selected from the group consisting of: 12.7°, 13.2°, 27.0° and 29.0°.

In another aspect, the methanesulfonate is identified by an X-ray powder diffraction pattern, obtained using Cu K alpha radiation, containing the following angle 2 theta values: 8.0°, 18.1° and 27.0°.

The citrate (ethanolate) is a crystalline salt of Compound A.

In one aspect, the citrate (ethanolate) is identified by an X-ray powder diffraction pattern, obtained using Cu K alpha radiation, containing the following angle 2 theta values: 6.4° and 14.6°.

In another aspect, the citrate (ethanolate) is identified by an X-ray powder diffraction pattern, obtained using Cu K alpha radiation, containing the following angle 2 theta values: 6.4° and 14.6°, and at least one angle 2 theta value selected from the group consisting of: 11.6°, 13.0°, 24.5° and 27.4°.

In another aspect, the citrate (ethanolate) is identified by an X-ray powder diffraction pattern, obtained using Cu K alpha radiation, containing the following angle 2 theta values: 6.4°, 14.6° and 24.5°.

The sulfate is a crystalline salt of Compound A.

In one aspect, the sulfate is identified by an X-ray powder diffraction pattern, obtained using Cu K alpha radiation, containing the following angle 2 theta values: 8.3° and 16.7°.

In another aspect, the sulfate is identified by an X-ray powder diffraction pattern, obtained using Cu K alpha radiation, containing the following angle 2 theta values: 8.3° and 16.7°, and at least one angle 2 theta value selected from the group consisting of: 4.1°, 12.5°, 15.7° and 23.0°.

In another aspect, the sulfate is identified by an X-ray powder diffraction pattern, obtained using Cu K alpha radiation, containing the following angle 2 theta values: 4.1°, 8.3° and 16.7°.

The benzenesulfonate (sesquihydrate) is a crystalline salt of Compound A.

In one aspect, the benzenesulfonate (sesquihydrate) is identified by an X-ray powder diffraction pattern, obtained using Cu K alpha radiation, containing the following angle 2 theta values: 6.7° and 12.8°.

In another aspect, the benzenesulfonate (sesquihydrate) is identified by an X-ray powder diffraction pattern, obtained using Cu K alpha radiation, containing the following angle 2 theta values: 6.7° and 12.8°, and at least one angle 2 theta value selected from the group consisting of: 9.6°, 15.1°, 19.2° and 20.7°.

In another aspect, the benzenesulfonate (sesquihydrate) is identified by an X-ray powder diffraction pattern, obtained using Cu K alpha radiation, containing the following angle 2 theta values: 6.7°, 12.8° and 19.2°.

The tosylate is a crystalline salt of Compound A.

In one aspect, the tosylate is identified by an X-ray powder diffraction pattern, obtained using Cu K alpha radiation, containing the following angle 2 theta values: 6.6° and 20.0°.

In another aspect, the tosylate is identified by an X-ray powder diffraction pattern, obtained using Cu K alpha radiation, containing the following angle 2 theta values: 6.6° and 20.0°, and at least one angle 2 theta value selected from the group consisting of: 9.8°, 13.2°, 14.5° and 19.2°.

In another aspect, the tosylate is identified by an X-ray powder diffraction pattern, obtained using Cu K alpha radiation, containing the following angle 2 theta values: 6.6°, 9.8° and 20.0°.

The fumarate (hemihydrate) is a crystalline salt of Compound A.

In one aspect, the fumarate (hemihydrate) is identified by an X-ray powder diffraction pattern, obtained using Cu K alpha radiation, containing the following angle 2 theta values: 7.2° and 14.5°.

In another aspect, the fumarate (hemihydrate) is identified by an X-ray powder diffraction pattern, obtained using Cu K alpha radiation, containing the following angle 2 theta values: 7.2° and 14.5°, and at least one angle 2 theta value selected from the group consisting of 6.0°, 15.9°, 23.5° and 26.0°.

In another aspect, the fumarate (hemihydrate) is identified by an X-ray powder diffraction pattern, obtained using Cu K alpha radiation, containing the following angle 2 theta values: 7.2°, 14.5° and 15.9°.

The phosphate is a crystalline salt of Compound A.

In one aspect, the phosphate is identified by an X-ray powder diffraction pattern, obtained using Cu K alpha radiation, containing the following angle 2 theta values: 9.9° and 15.5°.

In another aspect, the phosphate is identified by an X-ray powder diffraction pattern, obtained using Cu K alpha radiation, containing the following angle 2 theta values: 9.9° and 15.5°, and at least one angle 2 theta value selected from the group consisting of: 7.5°, 11.2°, 18.6° and 22.8°.

In another aspect, the phosphate is identified by an X-ray powder diffraction pattern, obtained using Cu K alpha radiation, containing the following angle 2 theta values: 9.9°, 15.5° and 18.6°.

The hydrobromide is a crystalline salt of Compound A.

In one aspect, the hydrobromide is identified by an X-ray powder diffraction pattern, obtained using Cu K alpha radiation, containing the following angle 2 theta values: 10.5° and 18.1°.

In another aspect, the hydrobromide is identified by an X-ray powder diffraction pattern, obtained using Cu K alpha radiation, containing the following angle 2 theta values: 10.5° and 18.1°, and at least one angle 2 theta value selected from the group consisting of: 16.0°, 16.6°, 23.8° and 28.2°.

In another aspect, the hydrobromide is identified by an X-ray powder diffraction pattern, obtained using Cu K alpha radiation, containing the following angle 2 theta values: 10.5°, 18.1° and 23.8°.

The L-malate is a crystalline salt of Compound A.

In one aspect, the L-malate is identified by an X-ray powder diffraction pattern, obtained using Cu K alpha radiation, containing the following angle 2 theta values: 23.0° and 25.1°.

In another aspect, the L-malate is identified by an X-ray powder diffraction pattern, obtained using Cu K alpha radiation, containing the following angle 2 theta values: 23.0° and 25.1°, and at least one angle 2 theta value selected from the group consisting of: 8.8°, 17.6°, 19.3° and 21.7°.

In another aspect, the L-malate is identified by an X-ray powder diffraction pattern, obtained using Cu K alpha radiation, containing the following angle 2 theta values: 19.3°, 23.0° and 25.1°.

The maleate FormA (hemihydrate) is a crystalline salt of Compound A.

In one aspect, the maleate FormA (hemihydrate) is identified by an X-ray powder diffraction pattern, obtained using Cu K alpha radiation, containing the following angle 2 theta values: 14.5° and 19.2°.

In another aspect, the maleate FormA (hemihydrate) is identified by an X-ray powder diffraction pattern, obtained using Cu K alpha radiation, containing the following angle 2 theta values: 14.5° and 19.2°, and at least one angle 2 theta value selected from the group consisting of: 8.8°, 11.4°, 21.1° and 21.9°.

In another aspect, the maleate FormA (hemihydrate) is identified by an X-ray powder diffraction pattern, obtained using Cu K alpha radiation, containing the following angle 2 theta values: 14.5°, 19.2° and 21.9°.

The maleate FormB is a crystalline salt of Compound A.

In one aspect, the maleate FormB is identified by an X-ray powder diffraction pattern, obtained using Cu K alpha radiation, containing the following angle 2 theta values: 17.2° and 23.8°.

In another aspect, the maleate FormB is identified by an X-ray powder diffraction pattern, obtained using Cu K alpha radiation, containing the following angle 2 theta values: 17.2° and 23.8°, and at least one angle 2 theta value selected from the group consisting of: 11.0°, 15.5°, 19.1° and 23.2°.

In another aspect, the maleate FormB is identified by an X-ray powder diffraction pattern, obtained using Cu K alpha radiation, containing the following angle 2 theta values: 17.2°, 23.2° and 23.8°.

The succinate is a crystalline salt of Compound A.

In one aspect, the succinate is identified by an X-ray powder diffraction pattern, obtained using Cu K alpha radiation, containing the following angle 2 theta values: 5.3° and 22.0°.

In another aspect, the succinate is identified by an X-ray powder diffraction pattern, obtained using Cu K alpha radiation, containing the following angle 2 theta values: 5.3° and 22.0°, and at least one angle 2 theta value selected from the group consisting of: 13.0°, 14.5°, 17.9° and 25.3°.

In another aspect, the succinate is identified by an X-ray powder diffraction pattern, obtained using Cu K alpha radiation, containing the following angle 2 theta values: 5.3°, 22.0° and 25.3°.

Form A is a polymorphic crystalline form of Compound A.

In one aspect, Form A is identified by an X-ray powder diffraction pattern, obtained using Cu K alpha radiation, containing the following angle 2 theta values: 13.8° and 26.4°.

In another aspect, Form A is identified by an X-ray powder diffraction pattern, obtained using Cu K alpha radiation, containing the following angle 2 theta values: 13.8° and 26.4°, and at least one angle 2 theta value selected from the group consisting of: 6.9°, 11.2°, 12.4°, 20.7° and 24.0°;

In another aspect, Form A is identified by an X-ray powder diffraction pattern, obtained using Cu K alpha radiation, containing the following angle 2 theta values: 13.8°, 26.4° and 11.2°.

Form D is a polymorphic crystalline form of Compound A.

In one aspect, Form D is identified by an X-ray powder diffraction pattern, obtained using Cu K alpha radiation, containing the following angle 2 theta values: 6.5° and 10.3°.

In another aspect, Form D is identified by an X-ray powder diffraction pattern, obtained using Cu K alpha radiation, containing the following angle 2 theta values: 6.5° and 10.3°, and at least one angle 2 theta value selected from the group consisting of: 9.3°, 14.6°, 18.7°, 19.5° and 22.2°.

In another aspect, Form D is identified by an X-ray powder diffraction pattern, obtained using Cu K alpha radiation, containing the following angle 2 theta values: 6.5°, 10.3° and 19.5°.

Form H is a polymorphic crystalline form of Compound A.

In one aspect, Form H is identified by an X-ray powder diffraction pattern, obtained using Cu K alpha radiation, containing the following angle 2 theta values: 5.8°, 11.5° and 11.6°.

In another aspect, Form H is identified by an X-ray powder diffraction pattern, obtained using Cu K alpha radiation, containing the following angle 2 theta values: 5.8°, 11.5° and 11.6°, and at least one angle 2 theta value selected from the group consisting of: 5.2°, 16.6°, 23.3° and 24.0°.

In another aspect, Form H is identified by an X-ray powder diffraction pattern, obtained using Cu K alpha radiation, containing the following angle 2 theta values: 5.8°, 11.5°, 11.6° and 16.6°.

Form G (monohydrate) is also identified by a differential scanning calorimetry (DSC) peak melting temperature of 124° C.

Form B is also identified by a differential scanning calorimetry (DSC) peak melting temperature of 181° C.

Form C (sesterhydrate) is also identified by a thermogravimetric and differential thermal analyses (TG-DTA) peak melting temperature of 131° C.

The hydrochloride is also identified by a differential scanning calorimetry (DSC) peak melting temperature of 295° C.

The methanesulfonate is also identified by a differential scanning calorimetry (DSC) peak melting temperature of 231° C.

Form A is also identified by a differential scanning calorimetry (DSC) peak melting temperature of 155° C.

Form D is also identified by a differential scanning calorimetry (DSC) peak melting temperature of 174° C.

Form H is also identified by a differential scanning calorimetry (DSC) peak melting temperature of 134° C.

Each form mentioned above may be identified by both of the X-ray powder diffraction pattern and the differential scanning calorimetry (DSC) peak melting temperature.

The numerical analysis to identify the various forms of the invention should be made objectively by considering that the values may include some experimental error depending on the measuring conditions. Therefore, the invention includes any forms substantially identified by the above-mentioned values for the identification.

In one aspect, the invention provides a process for preparing a crystalline Form G (monohydrate) of Compound A as defined above, which is characterized by using an alcohol solvate or anhydrous of Compound A as a raw material, dissolving the said alcohol solvate or anhydrous in an aqueous-organic mixed solvent, and crystallizing the intended crystalline Form G (monohydrate).

In one embodiment, the alcohol solvate or anhydrous of Compound A as a raw material in the above process is any amorphous or crystalline form of Compound A, or a mixture thereof, preferably any crystalline form of Compound A.

In one embodiment, the raw material used in the above process is an alcohol solvate, preferably an isopropanol or methanol solvate, more preferably isopropanol solvate of Compound A.

In another embodiment, the raw material used in the above process is a crystalline isopropanol solvate of Compound A.

In one embodiment, the aqueous-organic mixed solvent used in the above process to form the solution is a mixture of water and the solvent selected from the group consisting of alcohol, preferably methanol, ethanol, propanol, butanol or pentanol, more preferably ethanol; N,N-dimethylacetamide, N,N-dimethylformamide, isopropyl acetate, tert-butyl methyl ether and the mixture thereof.

In another embodiment, the aqueous-organic mixed solvent used in the above process to form the solution is a mixture of water and ethanol.

In one embodiment, the alcohol-water volume ratio is 50:50 to 10:90, preferably 20:50.

In one embodiment, the volume ratio of N,N-dimethylacetamide or N,N-dimethylformamide to water is 10-30%, preferably 20%. A small amount of water would be necessary when isopropyl acetate or tert-butyl methyl ether is used for the aqueous-organic mixed solvent.

In another aspect, the invention provides the process for preparing a crystalline Form G (monohydrate) of Compound A as defined above, which comprises the steps of:

(a) dissolving the isopropanol solvate of Compound A in a mixture of ethanol and water at 25-65° C., preferably 45-55° C. to form a solution;
(b) adding water to the solution of step (a) while keeping the temperature over 40° C., preferably 45-55° C.;
(c) seeding the solution of step (b) with one or more crystals of the intended crystalline Form G (monohydrate) over 40° C., preferably 45-55° C.;
(d) aging the solution of step (c) over 40° C., preferably 45-55° C. for over 1 hour; preferably 1-2 hours;
(e) adding water to the solution of step (d) for over 1 hour, preferably 1-2 hours at about 50° C., preferably 45-55° C. to form slurry;
(f) cooling the slurry of step (e) to ambient temperature id est 10-40° C., preferably 20-30° C.;
(g) aging the slurry of step (f) for over 0.5 hour, preferably 1-24 hours, more preferably overnight id est 8-16 hours at the same temperature as step (f);
(h) optionally further aging the slurry of step (g) below 5° C., preferably −5-5° C., preferably for over 0.5 hour, more preferably 1-2 hours; and
(i) collecting the crystals from the slurry of step (h).

In another aspect, the invention provides a crystalline form of Compound A as defined above, which is prepared by the above process.

The pharmaceutical test examples for Compound A are shown below.

Pharmaceutical Test 1 (Wee1 Kinase-inhibitory Effect)

(1) Purification of Wee1 Kinase:

A cDNA of Wee1 kinase with glutathione-S-transferase (GST) fused at the amino terminal thereof was inserted into a baculovirus expression vector to construct a recombinant baculovirus, with which cells of an insect cell line Sf9 were infected for high expression therein. The infected cells were recovered and solubilized, and then the GST-tagged Wee1 kinase protein was adsorbed by a glutathione column, and eluted from the column with glutathione, and the active fraction was desalted in a desalting column to give a purified enzyme.

(2) Determination of Wee1 Kinase Activity:

In determination of the Wee1 kinase activity, a synthetic peptide, Poly(Lys,Tyr) Hydrobromide (Lys:Tyr (4:1)) bought from Sigma was used as the substrate.

The amount of the reaction mixture was 21.1 μL; and the composition of the reaction buffer was 50 mM Tris-HCl buffer (pH 7.4)/10 mM magnesium chloride/1 mM dithiothreitol. The purified Wee1 kinase, 2.5 μg of the substrate peptide, 10 μM of non-labeled adenosine triphosphate (ATP) and 1 μCi of [γ-$^{33}$P]-labeled ATP (2500 Ci/mmol or more)

were added to it, and incubated at 30° C. for 30 minutes. Next, 10 μL of 350 mM phosphate buffer was added to the reaction mixture to stop the reaction. The substrate peptide was adsorbed by a P81 paper filter 96-well plate, then washed a few times with 130 mM phosphate buffer, and its radioactivity was counted with a liquid scintillation counter. The [γ-$^{33}$P]-labeled ATP was bought from Amersham Bioscience.

To add the test compound to the reaction system, the compound was diluted with dimethylsulfoxide (DMSO) to prepare a series of dilutions. 1.1 μL of each dilution was added to the reaction system. As a control, 1.1 μL of DMSO was added to the reaction system.

As a result, the half maximal inhibitory concentration ($IC_{50}$) value of Compound A obtained in Reference Example 2 was 11 nM.

Pharmaceutical Test 2 (Tumor Growth-Inhibitory Effect)

Human colon cancer cells WiDr (gotten from ATCC) were implanted into the subcutaneous area of the back of F344/N Jcl-rnu nude rats. Eight days after the implantation, gemcitabine (50 mg/kg, Gemzar injection, Eli-Lilly) was intravenously administered to them; and after 24 hours, a test compound was dissolved in a solvent (5% glucose) and given to them through continuous intravenous injection for 8 hours. The tumor volume (0.5×(major diameter)×(minor diameter)$^2$) was determined on day 0, 3, 6, 10 and 13. Day 0 means the day on which gemcitabine was administered. The relative tumor volume is a relative value, as calculated on the basis of the tumor volume of 1 on day 0. The tumor growth percentage (% T/C) was obtained according to the following formula: When the tumor volume change from day 0 in the group subjected to test compound administration is more than 0 (>0):

% T/C=[(tumor volume change in the test compounds on day 3, 6, 10, 13)/(tumor volume change in the control on day 3, 6, 10, 13)]×100.

When the tumor volume change from day 0 in the group subjected to test compound administration is less than 0 (<0):

% T/C=[(tumor volume change in the test compounds on day 3, 6, 10, 13)/(tumor volume change in the test compounds on day 0)]×100.

The data of the tumor growth-inhibiting effect are shown in Table 1.

TABLE 1

| | | % T/C | | | |
|---|---|---|---|---|---|
| Compound | n | day 3 | day 6 | day 10 | day 13 |
| Control | 4 | 100 | 100 | 100 | 100 |
| Gemcitabine 50 mg/kg | 4 | 22 | 31 | 54 | 65 |
| Compound A*[1], 0.75 mg/kg/hr | 3 | 86 | 74 | 81 | 89 |
| Gemcitabine + Compound A*[1], 0.5 mg/kg/hr | 3 | −1 | 3 | 24 | 43 |
| Gemcitabine + Compound A*[1], 0.75 mg/kg/hr | 4 | −20 | −37 | 2 | 14 |

Compound A*[1] was obtained in Reference Examlpe 2.

Gemcitabine administration reduced the tumor growth percentage, but when gemcitabine is combined with the compound of the invention, then the tumor growth percentage was further reduced. In particular, in the group where the chemical dose was high, the animals showed tumor involution.

As mentioned above, Compound A in combination with other anticancer agent augmented the effect of the other anticancer agent.

Pharmaceutical Test 3 (Method of Determining Drug Potency with Cells (Radiation (X-Ray) Sensitizing Effect))

a) Reagents:

Fetal bovine serum (FBS) was gotten from Morgate; RPMI 1640 medium and 0.25% trypsin EDTA were from Invitrogen; cycle test plus DNA reagent kit was from Becton Dickinson; and nylon net filter was from Millipore.

b) Cells:

Human non-small-cell lung cancer cells (NCI-H1299) were gotten from ATCC.

c) Method of effect determination:

NCI-H1299 cells were suspended in 10% FBS-added RPMI 1640 medium, and the cell suspension was applied to a 6-well Nunclondelta-processed plastic plate bought from Nunc, in an amount of 100,000 cell/2 ml/well, and incubated overnight in 5% $CO_2$-95% air at 37° C. Using Softex's M-150WE, the cells were irradiated with 5000 R X-rays, and then further incubated in 5% $CO_2$-95% air at 37° C. for 16 hours. A test compound was stepwise diluted with DMSO, and applied to a plate with the X-ray-processed cells sowed thereon, in an amount of 2 μL. This was incubated in 5% $CO_2$-95% air at 37° C. for 8 hours, and then the culture was partly taken out. 0.25% trypsin was added to the cells remaining on the plate, in an amount of 600 μL, and statically kept at room temperature to prepare a single cell suspension. The single cell suspension and the previously-taken culture were mixed for every sample, then centrifuged, and the supernatant was removed. Sampling was thus completed. The sample was suspended in a buffer (1 mL) of cycle test plus DNA reagent kid, and frozen and stored at −80° C. The stored sample was thawed on the test date, centrifuged and the supernatant was removed, and this was suspended in cycle test plus A solution (250 μL), left statically at room temperature for 10 minutes, and then B solution (150 μL) was added thereto and further kept statically at room temperature for 10 minutes. Next, C solution (150 μL) was added to it, kept statically at 4° C. for 10 minutes, and then filtered through nylon net filter to thereby complete DNA staining. Using Becton Dickinson's FACS Calibur, the DNA amount in each cell was quantitatively determined according to a FACS process, and the ratio of the cells having caused DNA fragmentation was determined.

TABLE 2

| DNA Fragmentation-Inducing Effect (H1299) (subG1, %) | | |
|---|---|---|
| X-ray | Compound A*[1] | X-ray + Compound A*[1] |
| 27.1 | 3.9 | 54.8 |

Compound A*[1] was obtained in Reference Examlpe 2.

As in Table 2, Compound A has an excellent DNA fragmentation-inducing effect to human-derived cancer cells (NCI-H1299).

As mentioned above, Compound A in combination with X-ray augmented the effect of the X-ray.

The novel crystalline forms of Compound A or a salt thereof, as well as Compound A per se, can be administered orally or parenterally, and after formulated into preparations suitable to such administration modes, the compounds can be used as pharmaceutical compositions or anticancer agents.

The term "cancer" as referred to in this description includes various sarcoma and carcinoma and includes solid cancer and hematopoietic cancer. The solid cancer as referred to herein includes, for example, brain tumor, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The novel crystalline forms of Compound A or a salt thereof, as well as Compound A per se, are expected to be effective especially for human solid cancer. The human solid cancer includes, for example, brain cancer, cervicocerebral cancer, esophageal cancer, thyroid cancer, small cell cancer, non-small cell cancer, breast cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia, Hodgkin's lymphoma.

The pharmaceutical composition or anticancer agent of the invention may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

With regard to each preparation of the pharmaceutical composition or anticancer agent of the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

The preparation can be prepared by a person having ordinary skill in the art according to conventional methods or common techniques. For example, a preparation can be carried out, if the preparation is an oral preparation, for example, by mixing an appropriate amount of the compound of the invention with an appropriate amount of lactose and filling this mixture into hard gelatin capsules which are suitable for oral administration. On the other hand, preparation can be carried out, if the preparation containing the compound of the invention is an injection, for example, by mixing an appropriate amount of the compound of the invention with an appropriate amount of 0.9% physiological saline and filling this mixture in vials for injection.

The novel crystalline forms of Compound A or a salt thereof, as well as Compound A per se, may be used, optionally in combination with any other agent useful for the treatment of various cancers or with radiotherapy. The individual ingredients for such combination may be administered at different times or at the same time as divided preparations or one preparation during the term of treatment. Accordingly, the invention should be so interpreted that it includes all modes of administration at the same time or at different times, and the administration in this invention should be interpreted so. The scope of the combination of the compound of the invention and any other agent useful for the above-mentioned diseases should include, in principle, any and all combinations thereof with any and all pharmaceutical agents useful for the treatment of the above-mentioned diseases.

Radiation therapy itself means an ordinary method in the field of treatment of cancer. For radiation therapy, various radiations such as X-ray, γ-ray, neutron ray, electron beam and proton beam; and radiation sources, can be used. In a most popular radiation therapy, a linear accelerator is used for irradiation with external radiations, γ-ray.

The novel crystalline forms of Compound A or a salt thereof, as well as Compound A per se, may be combined with a radiation therapy to enhance the therapeutical effect in radiation therapy; and therefore they may be useful as a radiation sensitizer in the field of treatment of cancer.

Another aspect of the novel crystalline forms of Compound A or a salt thereof, as well as Compound A per se, is that the compounds are also useful as a sensitizer for any other anticancer agents in the field of treatment of cancer.

The novel crystalline forms of Compound A or a salt thereof, as well as Compound A per se, may be combined with radiation therapy and/or combined with chemotherapy using any other anticancer agents described below in their use for treatment of cancer.

"Sensitizer" for radiation therapy or anticancer agent as referred to herein is meant to indicate a medical agent which, when used as combined with radiation therapy and/or chemotherapy with an anticancer agent, may additively or synergistically augment the therapeutical effect of that radiation therapy and/or chemotherapy.

The agents to be in the combined preparations in the invention may have any forms selected in any manner, and they may be produced in the same manner as that for the above-mentioned preparations. The combined agent comprising the compound of the invention and some other anticancer agent may be readily produced by a person skilled in the art according to ordinary methods or conventional techniques.

The above-mentioned combination includes not only the compositions of the invention that further contain one other active ingredient but also those further containing two or more other active substances. There are a lot of examples of the combination of the composition of the invention and one or two or more active substances selected from the pharmaceutical agents for the above-mentioned diseases.

The agents to be combined with the compositions include, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are cytarabine, gemcitabine and the like.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin, mitomycin C and the like.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are etoposide and the like.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato) platinum (II); ethylenediaminemalonatoplatinum (II); aqua (1,2-diaminodicyclohexane)sulfatoplatinum (II); aqua(1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is cisplatin. Further, other anticancer platinum coordination compounds mentioned in the specification are known and are commercially available and/or producible by a person having ordinary skill in the art by conventional techniques.

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a γ-phosphate group of ATP to a hydroxyl group of a specific tyrosine in protein. The term "anticancer tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other anticancer agent" as used in the specification refers to an anticancer agent which does not belong to any of the above-described agents having anticancer activities. Examples of the "other anticancer agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier" and "other anticancer agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from Glaxo-SmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following:

irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The invention also relates to a method for the treatment of cancer, which comprises administering to a subject in need thereof a therapeutically-effective amount of the crystalline form of Compound A or a salt thereof, which is selected from the group consisting of Form G (monohydrate), Form B, Form C (sesterhydrate), the hydrochloride, the methanesulfonate, the citrate (ethanolate), the sulfate, the benzenesulfonate (sesquihydrate), the tosylate, the fumarate (hemihydrate), the phosphate, the hydrobromide, the L-malate, the maleate Form A (hemihydrate), the maleate Form B and the succinate.

In the process according to the invention, preferred therapeutic unit may vary in accordance with, for example, the administration route of the compound of the invention, the type of the compound of the invention used, and the dosage form of the compound of the invention used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound of the invention may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with the compound of the invention is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m² or more. This dose is appropriately increased or decreased depending on the condition of the patient.

The therapeutic unit for gemcitabine is, for example, 1 g as gemcitabine/m² in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m² (body surface area) or less, and it may be appropriately increased or decreased within the range.

The therapeutic unit for etoposide is such that, for example, in the case of intravenous injection, 60 to 100 mg/m² (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m² (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m² (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m² (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m² is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

The invention is described more concretely with reference to the following Examples and Production Examples, which, however, are not intended to restrict the scope of the invention.

In thin-layer chromatography in Examples and Production Examples, Silica gel$_{60}$F$_{254}$ (Merck) was used for the plate, and a UV detector was used for detection. Wakogel™ C-300 or C-200 (Wako Pure Chemical Industries) or NH (Fuji Silysia Chemical) was used for column silica gel. In MS spectrometry, used was JMS-SX102A (JEOL) or QUATTROII (Micromass). In NMR spectrometry, dimethylsulfoxide was used as the internal standard in a heavy dimethylsulfoxide solution; a spectrometer of Gemini-300 (300 MHz; Varian), VXR-300 (300 MHz; Varian), Mercury 400 (400 MHz; Varian) or Inova 400 (400 MHz; Varian) was used; and all δ values are by ppm.

The meanings of the abbreviations in NMR are mentioned below.

s: singlet
d: doublet
dd: double doublet
t: triplet
dt: double triplet q: quartet
m: multiplet
br: broad
J: coupling constant
Hz: hertz
DMSO-$d_6$: heavy dimethylsulfoxide
THF: tetrahydrofuran The XRPD Patterns were collected on a BRUKER axs D8 ADVANCE. Copper K-Alpha 1 radiation at 35 kV, 40 mA was used. Samples were scanned between 5 and 40° 2 Theta at 0.1°/min. sec/step (step; 0.014, step time; 42.4 s). Intensity of X-ray diffraction was obtained as counts or counts per second in Y-axis. The intensities depend on not only degree of 2 theta but also amounts of a sample, crystallinity of a sample, crystalline form of a sample and salt form of a sample.

DSC thermograms were obtained using a TA instruments DSC Q1000. The experiments were run in a crimped aluminum pan with nitrogen flow. A sample was heated at 5° C./min from 25° C. to 200° C.

Thermogravimetric and Differential Thermal Analyses (TG-DTA) were conducted using a BRUKER axu TG-DTA 2000SA+MS 9600 system. A sample was heated at 10° C./min from 25° C. to 300° C. and a helium purge was used.

PRODUCTION EXAMPLE 1

Production of 2-allyl-6-(methylthio)-1,2-dihydro-3H-pyrazolo[3,4-d]pyrimidin-3-one 1) Tert-butyl 1-allylhydrazinecarboxylate:

250 g of tert-butyl hydrazinecarboxylate was added to toluene (3 L) solution of 280 g of phthalic anhydride. Using a Dean-Stark water separator, the reaction mixture was heated under reflux for 3 hours. This was cooled to room temperature, the formed solid was taken out through filtration to obtain 516 g of crude tert-butyl (1,3-dioxo-1,3-dihydro-2H-isoindol-2-yl)carbamate.

520 g of potassium carbonate, 43.3 g of benzyltriethylammonium chloride and 250 mL of allyl bromide were added in that order to acetonitrile (3.5 L) solution of the above compound, and stirred at room temperature for 18 hours. 1.5 L of water was added to the reaction solution, and the acetonitrile layer was separated and concentrated. One L of water was added to the residue and the aqueous layer, extracted with ethyl acetate, and the ethyl acetate layer was washed with saturated saline water, and then dried with anhydrous sodium sulfate. The solvent was evaporated away under reduced pressure, and the precipitated colorless solid was washed with hexane and dried to obtain 460 g of crude tert-butyl allyl(1,3-dioxo-1,3-dihydro-2H-isoindol-2-yl)carbamate.

With cooling in an ice bath, 100 mL of methylhydrazine was added to tetrahydrofuran (3.0 L) solution of the above compound, then restored to room temperature, and stirred for 18 hours. The precipitated insoluble matter was taken out through filtration, and the filtrate was concentrated. A mixed solvent of hexane/ethyl acetate (3/1) was added to the residue, and the precipitated insoluble matter was taken out through filtration. This operation was repeated five times, then the filtrate was concentrated under reduced pressure, the resulting residue was distilled under reduced pressure to obtain 211 g of the entitled compound as a pale yellow oily substance.
ESI-MS Found: m/z[M+H]+ 173.4.

2) Production of 2-allyl-6-(methylthio)-1,2-dihydro-3H-pyrazolo[3,4-d]pyrimidin-3-one:

260 mL of N,N-diisopropylethylamine and 106 g of the hydrazine obtained in the above 1 were added to tetrahydrofuran (1.5 L) solution of 142 g of ethyl 4-chloro-2-(methylthio)pyridine-5-carboxylate, and stirred with heating under reflux for 18 hours. After cooled to room temperature, the reaction solution was evaporated under reduced pressure, and 500 mL of diethyl ether was added to the residue, and the precipitated solid was separated through filtration. The filtrate was evaporated under reduced pressure, the residue was cooled in an ice bath, 400 mL of trifluoroacetic acid was gradually added thereto, and stirred at room temperature for 1 hour and then at 70° C. for 1 hour. The reaction solution was evaporated under reduced pressure, 500 mL of ethanol was added thereto and cooled in an ice bath, and 1.0 L of 6 N sodium hydroxide solution was added thereto and stirred at room temperature for 15 minutes. Cooled in an ice bath, the reaction solution was made acidic with 400 mL of concentrated hydrochloric acid, and then evaporated under reduced pressure. The residue was partitioned in chloroform and water, and the chloroform layer was extracted, washed with saturated saline water, and dried with anhydrous sodium sulfate. The solvent was evaporated away under reduced pressure, and the formed yellow solid was taken out through filtration, washed with ethanol and diethyl ether, and dried to obtain 99.1 g of the entitled compound as a yellow solid.
$^1$H-NMR (400 MHz, DMSO-$d_6$) δ: 8.66 (1.0H, brs), 5.83 (1.0H, ddt, J=17.1, 9.8, 5.4 Hz), 5.13 (1.0H, d, J=9.8 Hz), 5.06 (1.0H, d, J=17.1 Hz), 4.34 (2.0H, d, J=5.4 Hz), 2.51 (3.0H, s).
ESI-MS Found: m/z[M+H]+ 223.3.

REFERENCE EXAMPLE 1

Production of 2-allyl-6-(methylthio)-1-pyridin-2-yl-3H-pyrazolo[3,4-d]pyrimidin-3-one 2.4 mL of N,N'-dimethylethylenediamine was added to 1,4-dioxane (50 mL) solution of 4.44 g of 2-allyl-6-(methylthio)-1,2-dihydro-3H-pyrazolo[3,4-d]pyrimidin-3-one, 3.80 g of copper(I) iodide, 5.33 g of 2-iodopyridine and 3.80 g of potassium carbonate, and stirred overnight at 95° C. The reaction liquid was cooled, aqueous ammonia was added thereto and extracted with ethyl acetate, washed with saturated saline water and dried with anhydrous magnesium sulfate. The solvent was evaporated away under reduced pressure, and crystallized with ethyl acetate to obtain 5.15 g of the entitled compound as a white solid.
$^1$H-NMR (400 MHz, CDCl$_3$) δ: 8.94 (1H, s), 8.52 (1H, d, J=5.1 Hz), 7.90 (2H, d, J=3.5 Hz), 7.29-7.25 (1H, m), 5.68 (1H, ddt, J=17.0, 10.2, 6.3 Hz), 5.05 (1H, d, J=10.2 Hz), 4.91 (1H, d, J=17.0 Hz), 4.85 (1H, d, J=6.3 Hz), 2.58 (3H, s).
ESI-MS Found: m/z[M+H]+ 300.

REFERENCE EXAMPLE 2

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one 1) Production of 2-(6-bromo-2-pyridinyl)-2-propanol In a nitrogen atmosphere, 30 mL of 3 M methylmagnesium iodide/diethyl ether was added to 300 mL of diethyl ether solution of 8.72 g of methyl 6-bromopyridine-2-carboxylate. Water and 2 N hydrochloric acid were added to the reaction liquid, and extracted with ethyl acetate. This was washed with aqueous saturated sodium hydrogencarbonate solution and saturated saline water, and dried with anhydrous magnesium sulfate. The solvent was evaporated away under reduced pressure to obtain 8.51 g of crude 2-(6-bromo-2-pyridinyl)-2-propanol as a yellow oily substance.

$^1$H-NMR (400 MHz, CDCl$_3$) δ: 7.56 (1H, t, J=7.8 Hz), 7.38 (1H, dd, J=7.8, 1.0 Hz), 7.36 (1H, dd, J=7.8, 1.0 Hz), 1.55 (6H, s).

ESI-MS Found: m/z[M+H]+ 216, 218.

2) Production of 2-allyl-1-[6-(1-hydroxy-1-methyl-ethyl)-2-pyridinyl]-6-(methylthio)-1,2-dihydro-3H-pyrazolo[3,4-d]pyrimidin-3-one 12.89 g of the entitled compound was obtained in the same manner as in Reference Example 1, for which, however, the compound obtained in the above reaction was used in place of 2-iodopyridine used in Reference Example 1.

$^1$H-NMR (400 MHz, CDCl$_3$) δ: 8.95 (1H, s), 7.91 (1H, t, J=8.0 Hz), 7.76 (1H, d, J=7.3 Hz), 7.40 (1H, dd, J=7.8, 1.0 Hz), 5.70 (1H, ddt, J=17.1, 10.2, 6.3 Hz), 5.06 (1H, dd, J=10.2, 1.0 Hz), 4.93 (1H, dd, J=17.1, 1.2 Hz), 4.81 (2H, d, J=6.3 Hz), 2.59 (4H, s), 1.59 (6H, s).

ESI-MS Found: m/z[M+H]+:358.

3) Production of 2-allyl-1-[6-(1-hydroxy-1-methyl-ethyl)pyridin-2-yl]-6-{[4-(4-methylpiperazin-1-yl)phenyl]amino}-1,2-dihydro-3H-pyrazolo[3,4-d]pyrimidin-3-one 817 mg of m-chloroperbenzoic acid (>65%) was added to toluene (20 mL) solution of 1.10 g of the above produce, and stirred for 20 minutes. 1.61 mL of N,N-diisopropylethylamine and 706 mg of 4-(4-methylpiperazin-1-yl)aniline were added to the reaction liquid, and stirred overnight. Aqueous saturated sodium hydrogencarbonate solution was added to the reaction liquid, extracted with ethyl acetate, washed with saturated saline water, and dried with anhydrous magnesium sulfate. The solvent was evaporated away, and the residue was purified through basic silica gel column chromatography (hexane/ethyl acetate=1/1 to 0/1, ethyl acetate/ethanol=98/2). After concentrated, this was recrystallized from ethyl acetate to obtain 1.20 g of the entitled compound as a yellow solid.

$^1$H-NMR (400 MHz, CDCl$_3$) δ: 8.83 (1H, s), 7.86 (1H, dd, J=8.0, 7.8 Hz), 7.75 (1H, d, J=7.3 Hz), 7.49 (1H, brs), 7.48 (2H, d, J=9.0 Hz), 7.34 (1H, d, J=7.4 Hz), 6.93 (2H, d, J=9.0 Hz), 5.70 (1H, ddt, J=17.2, 10.0, 6.5 Hz), 5.04 (1H, d, J=10.0 Hz), 4.94 (1H, d, J=17.2 Hz), 4.74 (2H, d, J=6.5 Hz), 3.26 (4H, t, J=4.8 Hz), 2.73 (4H, brs), 2.44 (3H, s), 1.59 (6H, s).

ESI-MS Found: m/z[M+H]+ 501.

REFERENCE EXAMPLE 3

Production of Form A of Compound A 733 mg of m-chloroperbenzoic acid (>65%) was added to toluene (30 mL) solution of 1.02 g of 2-allyl-1-[6-(1-hydroxy-1-methylethyl)-2-pyridinyl]-6-(methylthio)-1,2-dihydro-3H-pyrazolo[3,4-d]pyrimidin-3-one, and stirred for 20 minutes. 1.45 mL of N,N-diisopropylethylamine and 710 mg of 4-(4-methylpiperazin-1-yl)aniline were added to the reaction liquid, and stirred overnight. Aqueous saturated sodium hydrogen carbonate solution was added to the reaction liquid, extracted with ethyl acetate, washed with brine, and dried with anhydrous magnesium sulfate. The solvent was evaporated away, and the residue was purified through basic silica gel column chromatography (hexane/ethyl acetate=1/1 to 0/1, ethyl acetate/ethanol=98/2). After concentrated, this was crystallized from ethyl acetate to obtain the entitled compound contaminated with a impurity. This impurity was removed by re-purified through basic silica gel column chromatography (hexane/ethyl acetate=1/1 to 0/1, ethyl acetate/ethanol=98/2) and collected the fractions not contaminated with the impurity. After concentrated, this was dissolved in ethyl acetate (10 mL) under reflux and the solution was stand over night in room temperature. The solid was collected by filtration and dried in vacuo to obtain 655 mg of the entitled compound as a yellow solid.

XRPD Patterns:
(2 theta (degrees), Intensity (cps)): (13.8°, 1039), (26.4°, 544), (6.9°, 162), (11.2°, 484), (12.4°, 135), (20.7°, 137), (24.0°, 151).

DSC:
When DSC of Form A was measured using a TA Instruments DSC Q1000 instrument, the extrapolated melting temperature onset of Form A was 154° C. with an enthalpy of fusion of 86.4 J/g at 5° C./min under nitrogen in crimped aluminum pan. The peak melting temperature was 155° C.

REFERENCE EXAMPLE 4

Production of Form D of Compound A 20.0 g of m-chloroperbenzoic acid (>65%) was added to toluene (500 mL) solution of 24.3 g of 2-allyl-1-[6-(1-hydroxy-1-methylethyl)-2-pyridinyl]-6-(methylthio)-1,2-dihydro-3H-pyrazolo[3,4-d]pyrimidin-3-one, and stirred for 40 minutes. 35.5 mL of N,N-diisopropylethylamine and 14.3 g of 4-(4-methylpiperazin-1-yl)aniline were added to the reaction liquid, and stirred overnight. Tetrahydrofuran (500 mL) and aqueous saturated sodium hydrogen carbonate solution were added to the reaction liquid, extracted with ethyl acetate, washed with brine, and dried with anhydrous magnesium sulfate. After the solvent was evaporated away, the solid was collected by filtration and washed with ethyl acetate to give 11.0 g of the crude entitle compound. The filtrate was concentrated and the residue was purified through silica gel column chromatography (hexane/ethyl acetate=1/1 to 0/1 and chloroform/methanol=1/0 to 7/1). After the solvent was evaporated away, the solid was collected by filtration and washed with ethyl acetate to give 16.9 g of the entitle compound. The filtrate was concentrated and the residue was purified through silica gel basic column chromatography (hexane/ethyl acetate=1/1 to 0/1, ethyl acetate/ethanol=98/2). After the solvent was evaporated away, the solid was collected by filtration and washed with ethyl acetate to give 2.50 g of the entitle compound. The combined crude title compounds (30.4 g) was recrystallized from isopropanol (300 mL) to obtain 32.2 g of the entitled compound as 1 isopropanol adduct. The entitled compound 1 isopropanol adduct (32.2 g) was dissolved in ethyl acetate (300 mL) under reflux and the solution was stirred over night in room temperature. The solid was collected by filtration and dried in vacuo to obtain 21.2 g of the entitled compound as a yellow solid.

XRPD Patterns:
(2 theta (degrees), Intensity (cps)): (6.5°, 71.0), (10.3°, 61.5), (9.3°, 40.8), (14.6°, 22.5), (18.7°, 22.0), (19.5°, 55.9), (22.2°, 32.2).

DSC:
When DSC of Form D was measured using a TA Instruments DSC Q1000 instrument, the extrapolated melting temperature onset of Form D was 173° C. with an enthalpy of fusion of 66.2 J/g at 5° C./min under nitrogen in crimped aluminum pan. The peak melting temperature was 174° C.

Before melting, a small endotherm peak with form conversion was detected at 135~150° C.

REFERENCE EXAMPLE 5

Production of Form H of Compound A 817 mg of m-chloroperbenzoic acid (>65%) was added to toluene (20 mL) solution of 1.10 g of 2-allyl-1-[6-(1-hydroxy-1-methylethyl)-2-pyridinyl]-6-(methylthio)-1,2-dihydro-3H-pyrazolo[3,4-d]pyrimidin-3-one, and stirred for 20 minutes. 1.61 mL of N,N-diisopropylethylamine and 706 mg of 4-(4-methylpiperazin-1-yl)aniline were added to the reaction liquid, and stirred overnight. Aqueous saturated sodium hydrogen carbonate solution was added to the reaction liquid, extracted with ethyl acetate, washed with brine, and dried with anhydrous magnesium sulfate. The solvent was evaporated away, and the residue was purified through silica gel column chromatography (hexane/ethyl acetate=1/1 to 0/1, ethyl acetate/ethanol=98/2, chloroform/methanol=10/1). After the solvent was evaporated away, the residue was re-purified through basic silica gel column chromatography (hexane/ethyl acetate=1/1 to 0/1, ethyl acetate/ethanol=98/2). After concentrated, this was dissolved in ethyl acetate under reflux and the solution was stand over night in room temperature. The solid was collected by filtration and dried in vacuo to obtain 1.20 g of the entitled compound as a yellow solid.

XRPD Patterns:
(2 theta (degrees), Intensity (cps)): (5.8°, 777), (11.5°, 189), (11.6°, 217), (5.2°, 133), (16.6°, 119), (23.3°, 80.9), (24.0°, 60.8).

DSC:
When DSC of Form H was measured using a TA Instruments DSC Q1000 instrument, the extrapolated melting temperature onset of Form H was 131° C. with an enthalpy of fusion of 43.1 J/g at 5° C./min under nitrogen in crimped aluminum pan. The peak melting temperature was 134° C. Before melting, a broad endotherm peak with form conversion was detected at ~100° C.

EXAMPLE 1

Production of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one monohydrate (Form G)

To a stirred solution of 2-allyl-1-[6-(1-hydroxy-1-methylethyl)-2-pyridinyl]-6-(methylthio)-1,2-dihydro-3H-pyrazolo[3,4-d]pyrimidin-3-one (2.17 g, 92.2 wt %, 2.00 g assay, 5.60 mmol) in toluene (30 mL) was added m-chloroperbenzoic acid (1.66 g) below 30° C. and the mixture was stirred at the same temperature for 30 minutes. Then N,N-diisopropylethylamine (2.92 mL) and 4-(4-methylpiperazin-1-yl) aniline (1.19 g) were added below 30° C. and the slurry was stirred at ambient temperature for more than 2 hours. Then toluene (30 mL) and isopropanol (50 mL) were added, and washed with aqueous 1N sodium hydroxide solution (20 mL) and 15% aqueous sodium chloride solution (10 mL). The aqueous layer was extracted with toluene (20 mL). The combined organic layers were concentrated to 40 mL and isopropanol (40 mL) was added. The mixture was concentrated to 40 mL and aged at ambient temperature for overnight. The crystal was collected by filtration, washed with isopropanol (20 mL) and dried in vacuo at ambient temperature for overnight to obtain the isopropanol solvate (2.99 g, 75.6 wt %) as a pale yellowish crystal in 81% yield.

Above isopropanol solvate (10.20 g, 78.4 wt %, 8.00 g assay, 15.98 mol) was dissolved in a mixture of ethanol (120 mL) and water (60 mL) at 50° C., and ethanol-water (2:1) (60 mL) was added. To the resulting solution was added water (160 mL) while keeping the temperature over 45° C. and the seed (80 mg) was added at 50° C. After aged at the same temperature for 1 hour, water (160 mL) was added over 1 hour at 50° C. Then the slurry was cooled to ambient temperature and aged for overnight. After aged below 5° C. for 1 hour, the crystal was collected by filtration, washed with ethanol-water (1:2.5) (80 mL) and dried in vacuo at ambient temperature for overnight to obtain 2-allyl-1-[6-(1-hydroxy-1-methylethyl) pyridin-2-yl]-6-{[4-(4-methylpiperazin-1-yl)phenyl] amino}-1,2-dihydro-3H-pyrazolo[3,4-d]pyrimidin-3-one monohydrate (7.97 g, 95.6 wt %) as a pale yellowish crystal in 95% yield. Melting Point: 124-126° C.

XRPD Patterns:
(2 theta (degrees), Intensity (cps)): (5.4°, 234), (5.9°, 1869), (11.5°, 527), (9.7°, 137), (12.8°, 79.7), (17.8°, 125), (20.5°, 84.9), (22.0°, 71.5), (23.8°, 67.7), (24.5°, 65.3), (25.0°, 47.5).

DSC:
When DSC of Form G was measured using a TA Instruments DSC Q1000 instrument, the extrapolated melting temperature onset of Form G was 121° C. with an enthalpy of fusion of 55.5 J/g at 2° C./min under nitrogen in crimped aluminum pan with pinhole. The peak melting temperature was 124° C. Before melting, a broad endotherm peak with dehydration was detected at ~115° C.

EXAMPLE 2

Production of Form B of Compound A 5 mg of Form A crystalline of Compound A was set on an aluminum plate. The plate was heated upto 170° C. at 5° C./min, then kept at 170° C. for 5 min., and finally cooled down room temperature at under nitrogen using Rigaku Thermo plus XRD-DSC II.

XRPD Patterns:
(2 theta (degrees), Intensity (cps)): (6.4°, 81.8), (6.5°, 78.1), (9.1°, 14.2), (10.2°, 37.4), (12.9°, 9.9), (18.8°, 31.3), (19.0°, 30.1).

DSC:
When DSC of Form A was measured using a TA Instruments DSC Q1000 instrument at 5° C./min under nitrogen in crimped aluminum pan, Form A melted at ~155° C. and then re-crystallized. The re-crystallized was Form B. When DSC of Form B was measured under same conditions above, the extrapolated melting temperature onset of Form B was 180° C. with an enthalpy of fusion of 47.8 J/g. The peak melting temperature was 181° C.

EXAMPLE 3

Production of Form C (Sesterhydrate) of Compound A 5 mg of Form A crystalline of Compound A was added to 1 ml of water. Using TAITEC Deep-well-maximizer, the mixture was mixed at room temperature for 24 hours. The mixture was centrifuged at 14,000 rpm for 10 minutes, and then the supernatant was removed. The residual solid was dried at room temperature for 5 days.

XRPD Patterns:
(2 theta (degrees), Intensity (cps)): (5.8°, 137), (11.2°, 58.6), (11.6°, 65.8), (18.2°, 41.1), (5.2°, 32.2), (13.8°, 36.6), (23.4°, 28.0).

Thermogravimetric and Differential Thermal Analyses (TG-DTA):
When TG-DTA of Form C was measured using a BRUKER axu TG-DTA 2000SA, the extrapolated melting temperature onset of Form C was 128° C. at 10° C./min heating under helium purge in open aluminum pan. The peak melting temperature was 131° C. Before melting, weight loss with dehydration was observed at ~125° C.

EXAMPLE 4

Production of Hydrochloride of Compound A 200 mg of Free base of the compound A was dissolved in 10 mL of methanol at 50° C. 0.24 mL of 2 mol/L HCl in ethanol was added to the resulting solution while keeping the temperature at 50° C. Then the slurry was cooled to ambient temperature and aged for overnight. The solid was collected by filtration, washed with methanol and dried in vacuo at 40° C. for 3 hrs to obtain 191 mg of the title hydrochloric acid salt as a crystal.

XRPD Patterns:
(2 theta (degrees), Intensity (cps)): (10.6°, 49.3), (16.7°, 45.7), (9.2°, 41.3), (9.9°, 40.2), (16.2°, 15.9), (18.3°, 41.6).

DSC:
When DSC of Hydrochloride was measured using a TA Instruments DSC Q1000 instrument, the extrapolated melting temperature onset of Hydrochloride was 293° C. with an enthalpy of fusion of 219 J/g at 10° C./min under nitrogen in crimped aluminum pan. The peak melting temperature was 295° C.

EXAMPLE 5

Production of Methansulfonate of Compound A 209 mg of Free base of the compound A suspended in 14.0 ml acetonitrile and suspension heated to about 60° C. until clear solution was obtained. Then added 0.8 mL of methanesulfonic acid stock solution (50 mg/ml in acetonitorile). About 60% of the solvent evaporated under nitrogen, then suspension stirred at room temperature for about 18 hours. Filtered and obtained yellowish solid dried under vacuum at 50° C. for about 60 hours.

XRPD Patterns:
(2 theta (degrees), Intensity (cps)): (8.0°, 48.2), (18.1°, 90.7), (12.7°, 65.5), (13.2°, 65.6), (27.0°, 57.5), (29.0°, 30.0).

DSC:
When DSC of Methanesulfonate was measured using a Perkin-elmer DSC 7 series, the extrapolated melting temperature onset of Methanesulfonate was 230° C. with an enthalpy of fusion of 106 J/g at 5° C./min under nitrogen in crimped pan. The peak melting temperature was 231° C.

EXAMPLE 6

Production of Citrate (Ethanolate) of Compound A 49.5 mg of Free base of the compound A suspended in 3.0 ml ethanol and suspension heated to about 60° C. until clear solution was obtained. To the clear solution was added 0.39 ml of citric acid stock solution (50 mg/ml). About 60% of the solvent evaporated under nitorogen, then suspension stirred at room temperature for about 18 hours. After separation of the solid by filtration the product was dried under vacuum at room temperature for about 60 hours.

XRPD Patterns:
(2 theta (degrees), Intensity (cps)): (6.4°, 142.3), (14.6°, 64.5), (11.6°, 36.2), (13.0°, 45.0), (24.5°, 57.6), (27.4°, 32.0).

EXAMPLE 7

Production of Sulfate of Compound A 100.4 mg of Free base of the compound A was dissolved in 8.0 ml acetonitrile at about 60° C. and to the clear solution was added 0.100 ml of 1M sulfuric acid. Obtained suspension stirred (open cap) for about 18 hours (about 60% of the solvent evaporated). After separation of the solid by filtration the product was dried under vacuum at room temperature for about 60 hours.

XRPD Patterns:
(2 theta (degrees), Intensity (cps)): (8.3°, 74.3), (16.7°, 96.6), (4.1°, 67.2), (12.5°, 64.5), (15.7°, 62.9), (23.0°, 63.6).

EXAMPLE 8

Production of Benzenesulfonate (Sesquihydrate) of Compound A 101 mg of Free base of the compound A (~0.2 mmol) was dissolved in 4.0 ml of acetonitrile/THF 3:1 (v/v) at about 40 to 50° C. and to the clear solution was added 31.82 mg of benzenesulfonic acid (~0.2 mmol) dissolved in 1.0 ml acetonitrile. The addition of this solution was carried out drop-wise under stirring, i.e., within about 5 to 10 minutes. The yellowish solution was cooled to ambient temperature and stirred in an open reaction tube at room temperature for about one day until most of the THF and part of the acetonitrile were evaporated. Then the suspension investigated by light microscopy which indicated that a crystalline product was obtained. After separation of the solid by filtration the product was dried under vacuum at 40° C. for about 16 hours. 88 mg of the titled benzenesulfonate (sesquihydrate) was obtained as a crystal.

XRPD Patterns:
(2 theta (degrees), Intensity (cps)): (6.7°, 49.0), (12.8°, 64.8), (9.6°, 34.4), (15.1°, 40.4), (19.2°, 44.6), (20.7°, 35.3).

EXAMPLE 9

Production of Tosylate of Compound A 103 mg of Free base of the compound A (~0.21 mmol) was dissolved in 4.0 ml of acetonitrile/THF 3:1 (v/v) at about 40 to 50° C. and to the clear solution was added 39.13 mg of toluenesulfonic acid (~0.21 mmol) dissolved in 1.0 ml acetonitrile. The addition of this solution was carried out drop-wise under stirring, i.e., within about 5 to 10 minutes. The yellowish solution was cooled to ambient temperature and stirred in an open reaction tube at room temperature for about one day until most of the THF and part of the acetonitrile were evaporated. Then the suspension was investigated by light microscopy which indicates that a crystalline product was obtained. After separation of the solid by filtration the product was dried under vacuum at 40° C. for about 16 hours. 109 mg of the titled tosylate was obtained as a crystal.

XRPD Patterns:
(2 theta (degrees), Intensity (cps)): (6.6°, 114.8), (20.0°, 101.7), (9.8°, 91.1), (13.2°, 86.5), (14.5°, 81.4), (19.2°, 75.1).

EXAMPLE 10

Production of Fumarate (Hemihydrate) of Compound A 97 mg of Free base of the compound A (~0.19 mmol) was dissolved in 3.0 ml of ethanol/THF 1:1 (v/v) at ambient temperature and to the clear solution was added 0.765 ml of a solution of fumaric acid in THF (29.5 mg/ml=0.19 mmol). The addition of this solution was carried out drop-wise under stirring, i.e., within about 5 to 10 minutes. This solution was slowly evaporated under nitrogen, and to the obtained solid residue 3.0 ml of acetonitrile was added and to obtained suspension was stirred at ambient temperature for about 20 hours. Then the suspension was investigated by light microscopy which indicated that a crystalline product was obtained. After separation of the solid by filtration the product was dried under vacuum at 40° C. for about 4 hours. XRPD Patterns:
(2 theta (degrees), Intensity (cps)): (7.2°, 79.2), (14.5°, 161.2), (6.0°, 46.3), (15.9°, 56.5), (23.5°, 49.4), (26.0°, 35.4).

EXAMPLE 11

Production of Phosphate of Compound A 104 mg of Free base of the compound A (~0.21 mmol) was dissolved in 4.0 ml of acetonitrile/THF 3:1 (v/v) at about 50° C. and to the clear solution was added 0.414 ml of 0.5M aqueous phosphoric acid. The addition of this solution was carried out drop-wise under stirring, i.e., within about 5 to 10 minutes. A fine yellowish suspension was obtained, which was stirred at ambient temperature for about three days. Then the suspension was investigated by light microscopy which indicated that a crystalline product was obtained. After separation of the solid by filtration the product was dried under vacuum at 40° C. for about 16 hours. 105 mg of the titled phosphate was obtained as a crystal.
XRPD Patterns:
(2 theta (degrees), Intensity (cps)): (9.9°, 81.7), (15.5°, 114.5), (7.5°, 50.6), (11.2°, 61.8), (18.6°, 80.7), (22.8°, 77.5).

EXAMPLE 12

Production of Hydrobromide of Compound A 100 mg of Free base of the compound A (~0.21 mmol) was dissolved in 4.0 ml of ethanol/ethyl acetate 1:1 (v/v) at about 40° C. and to the clear solution was added 0.400 ml of 0.5M aqueous hydrobromic acid. A fine yellowish suspension was obtained, which was stirred at ambient temperature for about one day. Then the suspension was investigated by light microscopy which indicated that a crystalline product is obtained. After separation of the solid by filtration the product was dried under vacuum at 40° C. for about 16 hours. About 98 mg of the titled hydrobromide was obtained as a crystal.
XRPD Patterns:
(2 theta (degrees), Intensity (cps)): (10.5°, 99.2), (18.1°, 72.0), (16.0°, 48.8), (16.6°, 50.2), (23.8°, 68.8), (28.2°, 61.8).

EXAMPLE 13

Production of L-Malate of Compound A 82 mg of Free base of the compound A (~0.17 mmol) was dissolved in 4.0 ml of acetonitrile at about 50° C. and to the clear solution was added 0.595 ml of L-malic acid solution in acetonitrile (37.3 mg/ml=0.17 mmol). The addition of this solution was carried out drop-wise under stirring, i.e., within about 5 to 10 minutes. Upon addition of the malic acid solution a fine suspension was formed which was stirred at ambient temperature for about one day. The reaction tube was stirred with the cap open for a few hours allowing to evaporate part of the solvent. After separation of the solid by filtration the product was dried under vacuum at 40° C. for about 22 hours. About 70 mg of the titled L-malate was obtained as a crystal.
XRPD Patterns:
(2 theta (degrees), Intensity (cps)): (23.0°, 172.6), (25.1°, 139.4), (8.8°, 66.4), (17.6°, 93.6), (19.3°, 100.2), (21.7°, 91.4).

EXAMPLE 14

Production of Maleate FormA (Hemihydrate) of Compound A 79 mg of Free base of the compound A (~0.16 mmol) was dissolved in 4.0 ml of acetonitrile at about 60° C. and to the clear solution was added 0.463 ml of maleic acid solution in acetonitrile (39.5 mg/ml=0.16 mmol). The addition of this solution was carried out drop-wise under stirring, i.e., within about 5 to 10 minutes. After several minutes a fine suspension is formed which was stirred at ambient temperature for about one day. The reaction tube was stirred with the cap open for a few hours allowing to evaporate part of the solvent. After separation of the solid by filtration the product was dried under vacuum at 40° C. for about 22 hours. About 79 mg of the titled maleate FormA was obtained as a crystal.
XRPD Patterns:
(2 theta (degrees), Intensity (cps)): (14.5°, 28.4), (19.2°, 29.1), (8.8°, 20.5), (11.4°, 19.7), (21.1°, 26.6), (21.9°, 28.0).

EXAMPLE 15

Production of Maleate FormB of Compound A 97 mg of Free base of the compound A (~0.19 mmol) was dissolved in 3.0 ml of THF/ethanol 1:1 at about 40° C. and to the clear solution was added 22.6 mg of maleic acid dissolved in 1.0 ml THF. This solution was slowly evaporated under a weak nitrogen flow at ambient temperature. To the obtained solid residue 1.0 ml of acetonitrile was added and the resulting suspension was stirred at ambient temperature for about 22 hours.
XRPD Patterns:
(2 theta (degrees), Intensity (cps)): (17.2°, 138.1), (23.8°, 133.9), (11.0°, 47.3), (15.5°, 47.0), (19.1°, 59.5), (23.2°, 68.5).

EXAMPLE 16

Production of Succinate of Compound A 107 mg of Free base of the compound A (~P0.21 mmol) was dissolved in 3.0 ml of THF/ethanol 1:1 at ambient temperature, and to the clear solution was added 0.574 ml of succinic acid solution in THF (44 mg/ml=0.16 mmol). The addition of this solution is carried out drop-wise under stirring, i.e., within about 5 to 10 minutes. This solution was slowly evaporated under a weak nitrogen flow at ambient temperature. To the obtained solid residue 1.0 ml of acetonitrile was added and the resulting suspension was stirred at ambient temperature for about 22 hours.

XRPD Patterns:

(2 theta (degrees), Intensity (cps)): (5.3°, 174.1), (22.0°, 93.7), (13.0°, 61.4), (14.5°, 73.4), (17.9°, 66.0), (25.3°, 98.3).

Industrial Applicability

The compounds of the invention have excellent Weel kinase-inhibitory effect and are therefore useful in the field of medicines, especially treatment of various cancers.

The invention claimed is:

1. Crystalline Form G (monohydrate) of Compound A:

Compound A

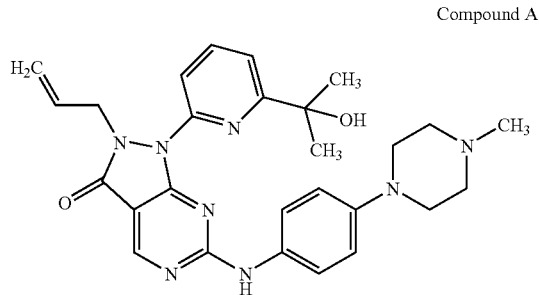

or a salt thereof,
having an X-ray powder diffraction pattern, obtained using Cu K alpha radiation, containing the following angle 2 theta values: 5.4°, 5.9° and 11.5°, and at least one angle 2 theta value selected from the group consisting of: 9.7°, 12.8°, 17.8°, 20.5°, 22.0°, 23.8°, 24.5° and 25.0°.

2. The crystalline form of claim 1, Form G (monohydrate), having a differential scanning calorimetry (DSC) peak melting temperature of 124° C.

3. A compound which is 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one monohydrate.

4. A pharmaceutical composition comprising a therapeutically-effective amount of the crystalline form of Compound A or a salt thereof as claimed in claim 1, and pharmaceutically acceptable carrier or diluent.

5. A process for preparing crystalline Form G (monohydrate) of Compound A as defined in claim 1, which is characterized by using an alcohol solvate or anhydrous of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one as a raw material, dissolving the said alcohol solvate or anhydrous in an aqueous-organic mixed solvent, and crystallizing the intended crystalline Form G (monohydrate).

6. The process of claim 5, which comprises the steps of:
(a) dissolving the isopropanol solvate of Compound A in a mixture of ethanol and water at 25-65° C. to form a solution;
(b) adding water to the solution of step (a) while keeping the temperature over 40° C.;
(c) seeding the solution of step (b) with one or more crystals of the intended crystalline Form G (monohydrate) over 40° C.;
(d) aging the solution of step (c) over 40° C. for over 1 hour;
(e) adding water to the solution of step (d) for over 1 hour at about 50° C. to form slurry;
(f) cooling the slurry of step (e) to ambient temperature;
(g) aging the slurry of step (f) for over 0.5 hour at the same temperature as step (f);
(h) optionally further aging the slurry of step (g) below 5° C. for over 0.5 hour; and
(i) collecting the crystals from the slurry of step (h).

7. A crystalline form of 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one, which is prepared by the process of claim 6.

8. A compound which is 2-allyl-1-[6-(1-hydroxy-1-methylethyl)pyridin-2-yl]-6-{[4-(4-methylpiperazin-1-yl)phenyl]amino}-1,2-dihydro-3H-pyrazolo[3,4-d]pyrimidin-3-one isopropanol solvate.

* * * * *